(12) United States Patent
Kerver et al.

(10) Patent No.: US 12,324,589 B2
(45) Date of Patent: Jun. 10, 2025

(54) SURGICAL INSTRUMENTS FOR APPLYING MULTIPLE CLIPS

(71) Applicant: INTUITIVE SURGICAL OPERATIONS, INC., Sunnyvale, CA (US)

(72) Inventors: Lawrence Kerver, San Jose, CA (US); Michael Blair Hurst, San Francisco, CA (US); Harsukhdeep Singh Ratia, Saratoga, CA (US); Craig Gerbi, Half Moon Bay, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 401 days.

(21) Appl. No.: 17/787,232

(22) PCT Filed: Jan. 6, 2021

(86) PCT No.: PCT/US2021/012284
§ 371 (c)(1),
(2) Date: Jun. 17, 2022

(87) PCT Pub. No.: WO2021/141971
PCT Pub. Date: Jul. 15, 2021

(65) Prior Publication Data
US 2023/0020577 A1  Jan. 19, 2023

Related U.S. Application Data

(60) Provisional application No. 62/958,195, filed on Jan. 7, 2020.

(51) Int. Cl.
A61B 17/128 (2006.01)
A61B 17/00 (2006.01)
(Continued)

(52) U.S. Cl.
CPC ...... *A61B 17/1285* (2013.01); *A61B 17/1222* (2013.01); *A61B 34/35* (2016.02); *A61B 2017/00398* (2013.01)

(58) Field of Classification Search
CPC . A61B 17/1285; A61B 17/1222; A61B 34/35; A61B 2017/00398
See application file for complete search history.

(56) References Cited

U.S. PATENT DOCUMENTS

| 75,364 A | 3/1868 | Case |
|---|---|---|
| 4,305,539 A | 12/1981 | Korolkov et al. |

(Continued)

FOREIGN PATENT DOCUMENTS

| CN | 103889344 A | 6/2014 |
|---|---|---|
| CN | 104042275 A | 9/2014 |

(Continued)

OTHER PUBLICATIONS

Supplementary European Search Report for Application No. EP19873128.3, mailed on Jun. 22, 2022, 7 pages.
(Continued)

*Primary Examiner* — Tan-Uyen T Ho
*Assistant Examiner* — Cherie M Poland
(74) *Attorney, Agent, or Firm* — Farber LLC

(57) ABSTRACT

A surgical instrument for applying surgical clips to tissue comprises an end effector having first and second jaws that are movable between open and closed positions and configured to receive first and second rows of clips in the open position. The instrument further includes an actuator coupled to the end effector and configured to move the jaws into the closed position and to discharge the first and second rows of clips. This allows an operator to apply multiple rows of clips to tissue with a single instrument insertion, which obviates the need to remove the surgical instrument from the
(Continued)

cannula to manually reload a new cartridge, thereby reducing the overall time of the surgical procedure.

20 Claims, 14 Drawing Sheets

(51) Int. Cl.
  *A61B 17/122* (2006.01)
  *A61B 34/35* (2016.01)

(56) References Cited

U.S. PATENT DOCUMENTS

| | | | |
|---|---|---|---|
| 4,319,576 A | 3/1982 | Rothfuss |
| 4,352,276 A | 10/1982 | Smith |
| 4,403,892 A | 9/1983 | Kane |
| 4,407,286 A | 10/1983 | Noiles et al. |
| 4,429,695 A | 2/1984 | Green |
| 4,509,518 A | 4/1985 | McGarry et al. |
| 4,509,932 A | 4/1985 | Weible |
| 4,605,001 A | 8/1986 | Rothfuss et al. |
| 4,608,981 A | 9/1986 | Rothfuss et al. |
| 4,610,383 A | 9/1986 | Rothfuss et al. |
| 4,633,874 A | 1/1987 | Chow et al. |
| 4,767,044 A | 8/1988 | Green |
| 4,809,695 A | 3/1989 | Gwathmey et al. |
| 4,848,637 A | 7/1989 | Pruitt |
| 4,892,244 A | 1/1990 | Fox et al. |
| 4,930,503 A | 6/1990 | Pruitt |
| 4,978,049 A | 12/1990 | Green |
| 5,027,834 A | 7/1991 | Pruitt |
| 5,040,715 A | 8/1991 | Green et al. |
| 5,133,735 A | 7/1992 | Slater et al. |
| 5,133,736 A | 7/1992 | Bales, Jr. et al. |
| 5,147,357 A | 9/1992 | Rose et al. |
| 5,180,092 A | 1/1993 | Crainich |
| 5,275,323 A | 1/1994 | Schulze et al. |
| 5,307,976 A | 5/1994 | Olson et al. |
| 5,312,023 A | 5/1994 | Green et al. |
| 5,334,183 A | 8/1994 | Wuchinich |
| 5,342,395 A | 8/1994 | Jarrett et al. |
| 5,342,396 A | 8/1994 | Cook |
| 5,366,133 A | 11/1994 | Geiste |
| 5,452,836 A | 9/1995 | Huitema et al. |
| 5,452,837 A | 9/1995 | Williamson, IV et al. |
| 5,465,895 A | 11/1995 | Knodel et al. |
| 5,480,089 A | 1/1996 | Blewett |
| 5,484,095 A | 1/1996 | Green et al. |
| 5,484,451 A | 1/1996 | Akopov et al. |
| 5,487,500 A | 1/1996 | Knodel et al. |
| 5,497,931 A | 3/1996 | Nakamura |
| 5,533,521 A | 7/1996 | Granger |
| 5,540,375 A | 7/1996 | Bolanos et al. |
| 5,554,164 A | 9/1996 | Wilson et al. |
| 5,560,530 A | 10/1996 | Bolanos et al. |
| 5,562,239 A | 10/1996 | Boiarski et al. |
| 5,564,615 A | 10/1996 | Bishop et al. |
| 5,571,116 A | 11/1996 | Bolanos et al. |
| 5,571,285 A | 11/1996 | Chow et al. |
| 5,573,534 A | 11/1996 | Stone |
| 5,615,820 A | 4/1997 | Viola |
| 5,624,452 A | 4/1997 | Yates |
| 5,628,446 A | 5/1997 | Geiste et al. |
| 5,651,491 A | 7/1997 | Heaton et al. |
| 5,652,849 A | 7/1997 | Conway et al. |
| 5,667,626 A | 9/1997 | Cayford et al. |
| 5,673,840 A | 10/1997 | Schulze et al. |
| 5,673,842 A | 10/1997 | Bittner et al. |
| 5,676,674 A | 10/1997 | Bolanos et al. |
| 5,688,269 A | 11/1997 | Newton et al. |
| 5,690,269 A | 11/1997 | Bolanos et al. |
| 5,693,042 A | 12/1997 | Boiarski et al. |
| 5,697,542 A | 12/1997 | Knodel et al. |
| 5,700,270 A | 12/1997 | Peyser et al. |
| 5,700,276 A | 12/1997 | Benecke |
| 5,709,680 A | 1/1998 | Yates et al. |
| 5,738,474 A | 4/1998 | Blewett |
| 5,752,644 A | 5/1998 | Bolanos et al. |
| 5,752,973 A | 5/1998 | Kieturakis et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,792,135 A | 8/1998 | Madhani et al. |
| 5,820,009 A | 10/1998 | Melling et al. |
| 5,826,776 A | 10/1998 | Schulze et al. |
| 5,833,695 A | 11/1998 | Yoon |
| 5,865,361 A | 2/1999 | Milliman et al. |
| 5,871,135 A | 2/1999 | Williamson, IV et al. |
| 5,911,353 A | 6/1999 | Bolanos et al. |
| 5,915,616 A | 6/1999 | Viola et al. |
| 5,919,198 A | 7/1999 | Graves, Jr. et al. |
| 5,941,442 A | 8/1999 | Geiste et al. |
| 5,954,259 A | 9/1999 | Viola et al. |
| 5,959,892 A | 9/1999 | Lin et al. |
| 6,032,849 A | 3/2000 | Mastri et al. |
| 6,050,996 A | 4/2000 | Schmaltz et al. |
| 6,079,606 A | 6/2000 | Milliman et al. |
| 6,126,666 A | 10/2000 | Trapp et al. |
| 6,174,309 B1 | 1/2001 | Wrublewski et al. |
| 6,202,914 B1 | 3/2001 | Geiste et al. |
| 6,241,139 B1 | 6/2001 | Milliman et al. |
| 6,250,532 B1 | 6/2001 | Green et al. |
| 6,330,956 B1 | 12/2001 | Willinger |
| 6,330,965 B1 | 12/2001 | Milliman et al. |
| 6,488,196 B1 | 12/2002 | Fenton, Jr. |
| 6,503,259 B2 | 1/2003 | Huxel et al. |
| 6,585,735 B1 | 7/2003 | Frazier et al. |
| 6,644,532 B2 | 11/2003 | Green et al. |
| 6,656,193 B2 | 12/2003 | Grant et al. |
| 6,669,073 B2 | 12/2003 | Milliman et al. |
| 6,786,382 B1 | 9/2004 | Hoffman |
| 6,817,974 B2 | 11/2004 | Cooper et al. |
| 6,877,647 B2 | 4/2005 | Green et al. |
| 6,905,057 B2 | 6/2005 | Swayze et al. |
| 6,953,139 B2 | 10/2005 | Milliman et al. |
| 6,959,852 B2 | 11/2005 | Shelton, IV et al. |
| 6,964,363 B2 | 11/2005 | Wales et al. |
| 6,978,921 B2 | 12/2005 | Shelton, IV et al. |
| 6,978,922 B2 | 12/2005 | Bilotti et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,000,819 B2 | 2/2006 | Swayze et al. |
| 7,044,352 B2 | 5/2006 | Shelton, IV et al. |
| 7,044,353 B2 | 5/2006 | Mastri et al. |
| 7,055,731 B2 | 6/2006 | Shelton, IV et al. |
| 7,059,508 B2 | 6/2006 | Shelton, IV et al. |
| 7,070,083 B2 | 7/2006 | Jankowski |
| 7,114,642 B2 | 10/2006 | Whitman |
| 7,128,253 B2 | 10/2006 | Mastri et al. |
| 7,140,527 B2 | 11/2006 | Ehrenfels et al. |
| 7,140,528 B2 | 11/2006 | Shelton, IV et al. |
| 7,258,262 B2 | 8/2007 | Mastri et al. |
| 7,308,998 B2 | 12/2007 | Mastri et al. |
| 7,328,828 B2 | 2/2008 | Ortiz et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,401,721 B2 | 7/2008 | Holsten et al. |
| 7,407,075 B2 | 8/2008 | Holsten et al. |
| 7,455,676 B2 | 11/2008 | Holsten et al. |
| 7,472,814 B2 | 1/2009 | Mastri et al. |
| 7,481,349 B2 | 1/2009 | Holsten et al. |
| 7,494,039 B2 | 2/2009 | Racenet et al. |
| 7,565,993 B2 | 7/2009 | Milliman et al. |
| 7,588,174 B2 | 9/2009 | Holsten et al. |
| 7,654,431 B2 | 2/2010 | Hueil et al. |
| 7,658,312 B2 | 2/2010 | Vidal et al. |
| 7,673,783 B2 | 3/2010 | Morgan et al. |
| 7,699,835 B2 | 4/2010 | Lee et al. |
| 7,721,930 B2 | 5/2010 | McKenna et al. |
| 7,726,539 B2 | 6/2010 | Holsten et al. |
| 7,770,774 B2 | 8/2010 | Mastri et al. |

(56) References Cited

U.S. PATENT DOCUMENTS

| | | |
|---|---|---|
| 7,794,475 B2 | 9/2010 | Hess et al. |
| 7,832,611 B2 | 11/2010 | Boyden et al. |
| 7,837,079 B2 | 11/2010 | Holsten et al. |
| 7,866,526 B2 | 1/2011 | Green et al. |
| 7,942,303 B2 | 5/2011 | Shah et al. |
| 7,950,561 B2 | 5/2011 | Aranyi |
| 8,070,035 B2 | 12/2011 | Holsten et al. |
| 8,083,118 B2 | 12/2011 | Milliman et al. |
| 8,127,975 B2 | 3/2012 | Olson et al. |
| 8,157,152 B2 | 4/2012 | Holsten et al. |
| 8,272,553 B2 | 9/2012 | Mastri et al. |
| 8,308,042 B2 | 11/2012 | Aranyi |
| 8,348,127 B2 | 1/2013 | Marczyk |
| 8,365,972 B2 | 2/2013 | Aranyi et al. |
| 8,371,492 B2 | 2/2013 | Aranyi et al. |
| 8,439,246 B1 | 5/2013 | Knodel |
| 8,490,851 B2 | 7/2013 | Blier et al. |
| 8,551,091 B2 | 10/2013 | Couture et al. |
| 8,573,465 B2 | 11/2013 | Shelton, IV |
| 8,579,178 B2 | 11/2013 | Holsten et al. |
| 8,608,047 B2 | 12/2013 | Holsten et al. |
| 8,672,206 B2 | 3/2014 | Aranyi et al. |
| 8,672,939 B2 | 3/2014 | Garrison |
| 8,701,960 B1 | 4/2014 | Manoux et al. |
| 8,783,541 B2 | 7/2014 | Shelton, IV et al. |
| 8,800,841 B2 | 8/2014 | Ellerhorst et al. |
| 8,834,518 B2 | 9/2014 | Faller et al. |
| 8,851,355 B2 | 10/2014 | Aranyi et al. |
| 8,852,174 B2 | 10/2014 | Burbank |
| 8,858,547 B2 | 10/2014 | Brogna |
| 8,864,010 B2 | 10/2014 | Williams |
| 8,905,287 B2 | 12/2014 | Racenet et al. |
| 8,925,785 B2 | 1/2015 | Holsten et al. |
| 9,010,606 B2 | 4/2015 | Aranyi et al. |
| 9,016,545 B2 | 4/2015 | Aranyi et al. |
| 9,055,961 B2 | 6/2015 | Manzo et al. |
| 9,192,378 B2 | 11/2015 | Aranyi et al. |
| 9,192,379 B2 | 11/2015 | Aranyi et al. |
| 9,211,120 B2 | 12/2015 | Scheib et al. |
| 9,216,019 B2 | 12/2015 | Schmid et al. |
| 9,307,986 B2 | 4/2016 | Hall et al. |
| 9,345,479 B2 | 5/2016 | Racenet et al. |
| 9,717,497 B2 | 8/2017 | Zerkle et al. |
| 9,717,498 B2 | 8/2017 | Aranyi et al. |
| 9,936,949 B2 | 4/2018 | Measamer et al. |
| 10,111,659 B2 | 10/2018 | Racenet et al. |
| 10,130,367 B2 | 11/2018 | Cappola et al. |
| 10,231,732 B1 | 3/2019 | Racenet et al. |
| 10,231,733 B2 | 3/2019 | Ehrenfels et al. |
| 10,285,693 B2 | 5/2019 | Kimsey et al. |
| 10,335,147 B2 | 7/2019 | Rector et al. |
| 10,363,037 B2 | 7/2019 | Aronhalt et al. |
| 10,646,219 B2 | 5/2020 | Racenet et al. |
| 10,828,027 B2 | 11/2020 | Racenet et al. |
| 10,863,988 B2 | 12/2020 | Patel et al. |
| 10,973,517 B2 | 4/2021 | Wixey |
| 11,234,700 B2 | 2/2022 | Ragosta et al. |
| 11,439,390 B2 | 9/2022 | Patel et al. |
| 11,504,124 B2 | 11/2022 | Patel et al. |
| 11,517,312 B2 | 12/2022 | Wixey |
| 11,642,129 B2 | 5/2023 | Burbank |
| 11,696,758 B2 | 7/2023 | Murphy et al. |
| 11,723,661 B2 | 8/2023 | Wixey et al. |
| 11,759,202 B2 | 9/2023 | Morgan et al. |
| 11,786,325 B2 | 10/2023 | Mustufa et al. |
| 11,806,015 B2 | 11/2023 | Wixey et al. |
| 11,857,188 B2 | 1/2024 | Hites |
| 11,864,762 B2 | 1/2024 | Wixey |
| 11,896,224 B2 | 2/2024 | Wellman |
| 11,944,301 B2 | 4/2024 | Wixey et al. |
| 11,944,302 B2 | 4/2024 | Wixey et al. |
| 11,986,184 B2 | 5/2024 | Patel et al. |
| 12,011,168 B2 | 6/2024 | Wixey |
| 12,029,426 B2 | 7/2024 | Millman et al. |
| 12,029,473 B2 | 7/2024 | Whitlock et al. |
| 2002/0165562 A1 | 11/2002 | Grant et al. |
| 2003/0135204 A1 | 7/2003 | Lee et al. |
| 2003/0181910 A1 | 9/2003 | Dycus et al. |
| 2004/0232199 A1 | 11/2004 | Shelton et al. |
| 2004/0267310 A1 | 12/2004 | Racenet et al. |
| 2005/0006430 A1 | 1/2005 | Wales |
| 2005/0006434 A1 | 1/2005 | Wales et al. |
| 2005/0070925 A1 | 3/2005 | Shelton, IV et al. |
| 2005/0070958 A1 | 3/2005 | Swayze et al. |
| 2005/0101991 A1 | 5/2005 | Ahlberg et al. |
| 2005/0113826 A1 | 5/2005 | Johnson et al. |
| 2005/0178813 A1 | 8/2005 | Swayze et al. |
| 2005/0187576 A1 | 8/2005 | Whitman et al. |
| 2005/0273084 A1 | 12/2005 | Hinman et al. |
| 2005/0273085 A1 | 12/2005 | Hinman et al. |
| 2006/0000868 A1 | 1/2006 | Shelton, IV et al. |
| 2006/0016853 A1 | 1/2006 | Racenet |
| 2006/0022014 A1 | 2/2006 | Shelton, IV et al. |
| 2006/0022015 A1 | 2/2006 | Shelton, IV et al. |
| 2006/0024817 A1 | 2/2006 | Deguchi et al. |
| 2006/0025809 A1 | 2/2006 | Shelton, IV |
| 2006/0025810 A1 | 2/2006 | Shelton, IV |
| 2006/0025811 A1 | 2/2006 | Shelton, IV |
| 2006/0025812 A1 | 2/2006 | Shelton, IV |
| 2006/0025813 A1 | 2/2006 | Shelton et al. |
| 2006/0025816 A1 | 2/2006 | Shelton, IV |
| 2006/0049230 A1 | 3/2006 | Shelton, IV et al. |
| 2006/0097026 A1 | 5/2006 | Shelton, IV |
| 2006/0111209 A1 | 5/2006 | Hinman et al. |
| 2006/0111210 A1 | 5/2006 | Hinman |
| 2006/0161190 A1 | 7/2006 | Gadberry et al. |
| 2006/0190031 A1 | 8/2006 | Wales et al. |
| 2006/0199999 A1 | 9/2006 | Ikeda et al. |
| 2006/0217706 A1 | 9/2006 | Lau et al. |
| 2006/0226196 A1 | 10/2006 | Hueil et al. |
| 2006/0271042 A1 | 11/2006 | Latterell et al. |
| 2007/0010838 A1 | 1/2007 | Shelton, IV et al. |
| 2007/0045379 A1 | 3/2007 | Shelton, IV |
| 2007/0250113 A1 | 10/2007 | Hegeman et al. |
| 2007/0262116 A1 | 11/2007 | Hueil et al. |
| 2008/0023522 A1 | 1/2008 | Olson et al. |
| 2008/0029577 A1 | 2/2008 | Shelton et al. |
| 2008/0078804 A1 | 4/2008 | Shelton et al. |
| 2008/0086114 A1 | 4/2008 | Schmitz et al. |
| 2008/0108446 A1 | 5/2008 | Faude |
| 2008/0196533 A1 | 8/2008 | Bergamasco et al. |
| 2008/0210738 A1 | 9/2008 | Shelton et al. |
| 2008/0308607 A1 | 12/2008 | Timm et al. |
| 2009/0277947 A1 | 11/2009 | Viola |
| 2010/0006620 A1 | 1/2010 | Sorrentino et al. |
| 2010/0076474 A1 | 3/2010 | Yates et al. |
| 2010/0108740 A1 | 5/2010 | Pastorelli et al. |
| 2010/0145334 A1 | 6/2010 | Olson et al. |
| 2010/0179545 A1 | 7/2010 | Twomey et al. |
| 2010/0198248 A1 | 8/2010 | Vakharia |
| 2010/0213240 A1 | 8/2010 | Kostrzewski |
| 2010/0331857 A1 | 12/2010 | Doyle et al. |
| 2011/0022078 A1 | 1/2011 | Hinman |
| 2011/0036891 A1 | 2/2011 | Zemlok et al. |
| 2011/0087238 A1 | 4/2011 | Wang et al. |
| 2011/0118707 A1 | 5/2011 | Burbank |
| 2011/0118778 A1 | 5/2011 | Burbank |
| 2011/0121050 A1 | 5/2011 | Nicholas et al. |
| 2011/0152879 A1 | 6/2011 | Williams |
| 2011/0174863 A1 | 7/2011 | Shelton, IV et al. |
| 2011/0186614 A1 | 8/2011 | Kasvikis |
| 2011/0251612 A1 | 10/2011 | Faller et al. |
| 2011/0251613 A1 | 10/2011 | Guerra et al. |
| 2011/0288573 A1 | 11/2011 | Yates et al. |
| 2011/0290851 A1 | 12/2011 | Shelton, IV |
| 2011/0290853 A1 | 12/2011 | Shelton, IV et al. |
| 2011/0290854 A1 | 12/2011 | Timm et al. |
| 2011/0295270 A1 | 12/2011 | Giordano et al. |
| 2011/0301603 A1 | 12/2011 | Kerr et al. |
| 2012/0000962 A1 | 1/2012 | Racenet et al. |
| 2012/0022584 A1 | 1/2012 | Donnigan et al. |
| 2012/0071891 A1 | 3/2012 | Itkowitz et al. |
| 2012/0205419 A1 | 8/2012 | Weir et al. |
| 2012/0223121 A1 | 9/2012 | Viola et al. |

(56) References Cited

U.S. PATENT DOCUMENTS

| | | |
|---|---|---|
| 2012/0228358 A1 | 9/2012 | Zemlok et al. |
| 2012/0248167 A1 | 10/2012 | Flanagan et al. |
| 2012/0255986 A1 | 10/2012 | Petty et al. |
| 2012/0289999 A1 | 11/2012 | Frank |
| 2012/0298719 A1 | 11/2012 | Shelton, IV et al. |
| 2013/0015231 A1 | 1/2013 | Kostrzewski |
| 2013/0046303 A1 | 2/2013 | Evans et al. |
| 2013/0056521 A1 | 3/2013 | Swensgard |
| 2013/0068821 A1 | 3/2013 | Huitema et al. |
| 2013/0087599 A1 | 4/2013 | Krumanaker et al. |
| 2013/0098965 A1 | 4/2013 | Kostrzewski et al. |
| 2013/0126586 A1 | 5/2013 | Zhang et al. |
| 2013/0148577 A1 | 6/2013 | Terry et al. |
| 2013/0248577 A1 | 9/2013 | Leimbach et al. |
| 2013/0277410 A1 | 10/2013 | Fernandez et al. |
| 2013/0296922 A1 | 11/2013 | Allen, IV et al. |
| 2013/0327808 A1 | 12/2013 | Chen et al. |
| 2014/0001236 A1 | 1/2014 | Shelton, IV et al. |
| 2014/0005653 A1 | 1/2014 | Shelton, IV et al. |
| 2014/0021239 A1 | 1/2014 | Kostrzewski |
| 2014/0025071 A1 | 1/2014 | Sims et al. |
| 2014/0027492 A1 | 1/2014 | Williams |
| 2014/0100600 A1 | 4/2014 | Kendrick |
| 2014/0103093 A1 | 4/2014 | Koch, Jr. et al. |
| 2014/0110455 A1 | 4/2014 | Ingmanson et al. |
| 2014/0175152 A1 | 6/2014 | Hess et al. |
| 2014/0180286 A1 | 6/2014 | Marczyk et al. |
| 2014/0183244 A1 | 7/2014 | Duque et al. |
| 2014/0200596 A1 | 7/2014 | Weir et al. |
| 2014/0200612 A1 | 7/2014 | Weir et al. |
| 2014/0200851 A1 | 7/2014 | Weir et al. |
| 2014/0214049 A1 | 7/2014 | Jeong et al. |
| 2014/0239036 A1 | 8/2014 | Zerkle et al. |
| 2014/0239044 A1 | 8/2014 | Hoffman |
| 2014/0246477 A1 | 9/2014 | Koch, Jr. et al. |
| 2014/0249557 A1 | 9/2014 | Koch, Jr. et al. |
| 2014/0257331 A1 | 9/2014 | Kim et al. |
| 2014/0263546 A1 | 9/2014 | Aranyi |
| 2014/0263552 A1 | 9/2014 | Hall et al. |
| 2014/0263559 A1 | 9/2014 | Williams et al. |
| 2014/0263567 A1 | 9/2014 | Williams et al. |
| 2014/0263569 A1 | 9/2014 | Williams et al. |
| 2014/0284372 A1 | 9/2014 | Kostrzewski |
| 2014/0305989 A1 | 10/2014 | Parihar et al. |
| 2014/0343550 A1 | 11/2014 | Faller et al. |
| 2014/0343569 A1 | 11/2014 | Turner |
| 2014/0364851 A1 | 12/2014 | Batross et al. |
| 2015/0073746 A1 | 3/2015 | Gris et al. |
| 2015/0173756 A1 | 6/2015 | Baxter, III et al. |
| 2015/0173789 A1 | 6/2015 | Baxter, III et al. |
| 2015/0209030 A1 | 7/2015 | Kostrzewski et al. |
| 2015/0209037 A1 | 7/2015 | Kostrzewski et al. |
| 2015/0250530 A1 | 9/2015 | Manzo et al. |
| 2015/0256609 A1 | 9/2015 | Morton et al. |
| 2015/0272575 A1 | 10/2015 | Leimbach et al. |
| 2015/0272576 A1 | 10/2015 | Cappola |
| 2015/0297227 A1 | 10/2015 | Huitema et al. |
| 2015/0297230 A1 | 10/2015 | Schellin et al. |
| 2015/0297235 A1 | 10/2015 | Harris et al. |
| 2015/0369277 A1 | 12/2015 | Fevre et al. |
| 2016/0038227 A1 | 2/2016 | Garrison |
| 2016/0058450 A1 | 3/2016 | Shelton, IV et al. |
| 2016/0066916 A1 | 3/2016 | Overmyer et al. |
| 2016/0089148 A1 | 3/2016 | Harris et al. |
| 2016/0120544 A1 | 5/2016 | Shelton, IV et al. |
| 2016/0157863 A1 | 6/2016 | Williams et al. |
| 2016/0174977 A1 | 6/2016 | Lytle, IV et al. |
| 2016/0175033 A1 | 6/2016 | Le |
| 2016/0192999 A1 | 7/2016 | Stulen et al. |
| 2016/0235489 A1 | 8/2016 | Gombert et al. |
| 2016/0242782 A1 | 8/2016 | Shelton, IV et al. |
| 2016/0249921 A1 | 9/2016 | Cappola et al. |
| 2016/0270780 A1 | 9/2016 | Hall et al. |
| 2016/0287251 A1 | 10/2016 | Shelton, IV et al. |
| 2016/0296226 A1 | 10/2016 | Kostrzewski |
| 2016/0338764 A1 | 11/2016 | Krastins et al. |
| 2017/0010578 A1 | 1/2017 | Miyakawa |
| 2017/0042604 A1 | 2/2017 | McFarland et al. |
| 2017/0056098 A1 | 3/2017 | Crews et al. |
| 2017/0079710 A1 | 3/2017 | Deville et al. |
| 2017/0097035 A1 | 4/2017 | Zimmerman et al. |
| 2017/0135746 A1 | 5/2017 | Tetzlaff et al. |
| 2017/0143335 A1 | 5/2017 | Gupta et al. |
| 2017/0189028 A1 | 7/2017 | Aranyi |
| 2017/0231653 A1 | 8/2017 | Kapadia |
| 2017/0245857 A1 | 8/2017 | Shelton, IV et al. |
| 2017/0290584 A1 | 10/2017 | Jasemian et al. |
| 2017/0296172 A1 | 10/2017 | Harris et al. |
| 2017/0296173 A1 | 10/2017 | Shelton, IV et al. |
| 2018/0008265 A1 | 1/2018 | Hatanaka et al. |
| 2018/0021042 A1 | 1/2018 | Nicholas et al. |
| 2018/0161052 A1 | 6/2018 | Weir et al. |
| 2018/0168581 A1 | 6/2018 | Hunter et al. |
| 2018/0168585 A1 | 6/2018 | Shelton, IV et al. |
| 2018/0168622 A1 | 6/2018 | Shelton, IV et al. |
| 2018/0168628 A1 | 6/2018 | Hunter et al. |
| 2018/0168637 A1 | 6/2018 | Harris et al. |
| 2018/0168641 A1 | 6/2018 | Harris et al. |
| 2018/0168642 A1 | 6/2018 | Shelton, IV et al. |
| 2018/0168644 A1 | 6/2018 | Shelton, IV et al. |
| 2018/0168649 A1 | 6/2018 | Shelton, IV et al. |
| 2018/0168650 A1 | 6/2018 | Shelton, IV et al. |
| 2018/0206844 A1 | 7/2018 | Harris et al. |
| 2018/0214200 A1 | 8/2018 | Nanditale et al. |
| 2018/0232951 A1 | 8/2018 | Alterovitz et al. |
| 2018/0296213 A1 | 10/2018 | Strobl |
| 2018/0310935 A1 | 11/2018 | Wixey |
| 2018/0310948 A1 | 11/2018 | Stamm et al. |
| 2018/0317915 A1 | 11/2018 | McDonald, II |
| 2019/0000454 A1 | 1/2019 | Swayze |
| 2019/0015124 A1 | 1/2019 | Williams et al. |
| 2019/0059894 A1 | 2/2019 | Kumada et al. |
| 2019/0076143 A1 | 3/2019 | Smith |
| 2019/0083086 A1 | 3/2019 | Klaffenböck et al. |
| 2019/0099181 A1 | 4/2019 | Shelton, IV et al. |
| 2019/0125347 A1 | 5/2019 | Stokes et al. |
| 2019/0133571 A1 | 5/2019 | Racenet et al. |
| 2019/0142531 A1 | 5/2019 | Wentworth et al. |
| 2019/0192137 A1 | 6/2019 | Shelton, IV et al. |
| 2019/0201146 A1 | 7/2019 | Shelton, IV et al. |
| 2019/0231350 A1* | 8/2019 | Scott .................. A61B 17/083 |
| 2019/0239881 A1 | 8/2019 | Laurent et al. |
| 2019/0290374 A1 | 9/2019 | Ramadorai |
| 2019/0298346 A1 | 10/2019 | Shelton, IV et al. |
| 2019/0298356 A1 | 10/2019 | Shelton, IV et al. |
| 2019/0314107 A1 | 10/2019 | Worrell et al. |
| 2019/0365458 A1 | 12/2019 | Whitlock et al. |
| 2020/0205811 A1 | 7/2020 | Posey et al. |
| 2020/0397430 A1 | 12/2020 | Patel et al. |
| 2021/0000557 A1 | 1/2021 | Mustufa et al. |
| 2021/0022736 A1 | 1/2021 | Wixey |
| 2021/0077101 A1 | 3/2021 | Patel et al. |
| 2021/0161529 A1 | 6/2021 | Wixey |
| 2021/0177412 A1 | 6/2021 | Wilson et al. |
| 2021/0177495 A1 | 6/2021 | Ross et al. |
| 2021/0177500 A1 | 6/2021 | Khalaji |
| 2021/0212683 A1 | 7/2021 | Burbank |
| 2021/0236119 A1 | 8/2021 | Chavan et al. |
| 2021/0267596 A1 | 9/2021 | Fanelli et al. |
| 2021/0386427 A1 | 12/2021 | Millman et al. |
| 2022/0015762 A1 | 1/2022 | Wixey et al. |
| 2022/0015763 A1 | 1/2022 | Wixey et al. |
| 2022/0015823 A1 | 1/2022 | Wilson et al. |
| 2022/0054130 A1 | 2/2022 | Overmyer et al. |
| 2022/0061836 A1 | 3/2022 | Parihar et al. |
| 2022/0061840 A1 | 3/2022 | Hites |
| 2022/0061841 A1 | 3/2022 | Wixey et al. |
| 2022/0071632 A1 | 3/2022 | Patel et al. |
| 2022/0079585 A1 | 3/2022 | Egan |
| 2022/0125428 A1 | 4/2022 | Ragosta et al. |
| 2022/0160358 A1 | 5/2022 | Wixey |
| 2022/0167985 A1 | 6/2022 | George et al. |
| 2022/0183686 A1 | 6/2022 | Wixey et al. |
| 2022/0192665 A1 | 6/2022 | Wellman |

(56) References Cited

U.S. PATENT DOCUMENTS

| | | |
|---|---|---|
| 2022/0346790 A1 | 11/2022 | Wellman |
| 2022/0378537 A1 | 12/2022 | Hites et al. |
| 2022/0395270 A1 | 12/2022 | Patel et al. |
| 2023/0047784 A1 | 2/2023 | Patel et al. |
| 2023/0052074 A1 | 2/2023 | Wixey |
| 2023/0101993 A1 | 3/2023 | Baril et al. |
| 2023/0210527 A1 | 7/2023 | Shelton, IV et al. |
| 2023/0225731 A1 | 7/2023 | Burbank |
| 2023/0329711 A1 | 10/2023 | Wixey et al. |
| 2024/0023961 A1 | 1/2024 | Wixey et al. |
| 2024/0065690 A1 | 2/2024 | Jasemian et al. |
| 2024/0081824 A1 | 3/2024 | Hites |
| 2024/0108343 A1 | 4/2024 | Wixey |
| 2024/0138834 A1 | 5/2024 | Wellman |
| 2024/0252171 A1 | 8/2024 | Wixey et al. |
| 2024/0260959 A1 | 8/2024 | Wixey et al. |

FOREIGN PATENT DOCUMENTS

| | | |
|---|---|---|
| CN | 105007836 A | 10/2015 |
| CN | 106232026 A | 12/2016 |
| CN | 107920819 A | 4/2018 |
| CN | 108024809 A | 5/2018 |
| CN | 112165909 A | 1/2021 |
| DE | 694747 C | 8/1940 |
| DE | 3724525 C1 | 5/1988 |
| EP | 0277532 B1 | 8/1990 |
| EP | 0469396 A1 | 2/1992 |
| EP | 0277529 B1 | 4/1993 |
| EP | 0641546 A1 | 3/1995 |
| EP | 1090592 A1 | 4/2001 |
| EP | 1479348 A1 | 11/2004 |
| EP | 1728473 A1 | 12/2006 |
| EP | 1479346 B1 | 1/2007 |
| EP | 1621141 B1 | 7/2007 |
| EP | 2374419 A2 | 10/2011 |
| EP | 1316290 B1 | 2/2012 |
| EP | 2517639 A1 | 10/2012 |
| EP | 2540231 A2 | 1/2013 |
| EP | 1754445 B1 | 10/2013 |
| EP | 2777529 A1 | 9/2014 |
| EP | 2777530 A1 | 9/2014 |
| EP | 2777532 A2 | 9/2014 |
| EP | 2944275 A2 | 11/2015 |
| EP | 2992834 A1 | 3/2016 |
| EP | 3000408 A2 | 3/2016 |
| EP | 3120780 A2 | 1/2017 |
| EP | 3135225 A2 | 3/2017 |
| EP | 3158947 A1 | 4/2017 |
| EP | 3173029 A1 | 5/2017 |
| EP | 3205291 A1 | 8/2017 |
| EP | 3338703 A1 | 6/2018 |
| FR | 2828952 B1 | 12/2005 |
| JP | S5794132 A | 6/1982 |
| JP | 5301166 B2 | 9/2013 |
| JP | 2014530653 A | 11/2014 |
| JP | 2016508792 A | 3/2016 |
| JP | 2016513570 A | 5/2016 |
| JP | 2017500146 A | 1/2017 |
| JP | 2017513564 A | 6/2017 |
| JP | 2017527396 A | 9/2017 |
| JP | 6411461 B2 | 10/2018 |
| JP | 2019141659 A | 8/2019 |
| SU | 405234 A1 | 9/1975 |
| SU | 886900 A1 | 12/1981 |
| SU | 1333319 A2 | 8/1987 |
| SU | 1442191 A1 | 12/1988 |
| SU | 1459659 A1 | 2/1989 |
| WO | WO-8602254 A1 | 4/1986 |
| WO | WO-9005489 A1 | 5/1990 |
| WO | WO-9734533 A1 | 9/1997 |
| WO | WO-03094743 A1 | 11/2003 |
| WO | WO-03094746 A1 | 11/2003 |
| WO | WO-03094747 A1 | 11/2003 |
| WO | WO-2004020859 A1 | 3/2004 |
| WO | WO-2012142872 A1 | 10/2012 |
| WO | WO-2014106275 A1 | 7/2014 |
| WO | WO-2017026141 A1 | 2/2017 |
| WO | WO-2017034803 A2 | 3/2017 |
| WO | WO-2017156070 A1 | 9/2017 |
| WO | WO-2017214243 A1 | 12/2017 |
| WO | WO-2018005750 A1 | 1/2018 |
| WO | WO-2018071497 A1 | 4/2018 |
| WO | WO-2018118402 A1 | 6/2018 |
| WO | WO-2019090047 A1 | 5/2019 |
| WO | WO-2020081960 A1 | 4/2020 |
| WO | WO-2020131692 A1 | 6/2020 |

OTHER PUBLICATIONS

Anonymous: "Slip Joint Pliers—Wikipedia," Sep. 2017, 1 Pages. Retrieved from internet URL:https://en.wikipedia.org/w/index.php?tilte=split_joint_pliers&oldid=801407143.

Extended European Search Report for Application No. EP19757451.0, mailed on May 19, 2022, 16 pages.

Extended European Search Report for Application No. EP19898247.2, mailed on Jan. 10, 2023, 12 pages.

Extended European Search Report for Application No. EP19900059.7, mailed on Dec. 5, 2022, 10 pages.

Extended European Search Report for Application No. EP20790773.4, mailed on Nov. 29, 2022, 09 pages.

Extended European Search Report for Application No. EP20815112.6, mailed on Jan. 5, 2023, 11 pages.

Extended European Search Report for Application No. EP20875978.7, mailed on Jan. 31, 2024, 26 pages.

Extended European Search Report for Application No. EP24155564.8, mailed on Jul. 8, 2024, 12 pages.

European Search Report (Corrected version) for Application No. EP19750317.0, mailed on Mar. 28, 2022, 26 pages.

International Search Report and Written Opinion for Application No. PCT/US2020/054568, mailed Jan. 29, 2021, 13 pages.

International Preliminary Report on Patentability for Application No. PCT/US2019/017646, mailed on Aug. 27, 2020, 10 pages.

International Preliminary Report on Patentability for Application No. PCT/US2019/019501, mailed Sep. 3, 2020, 7 pages.

International Search Report and Written Opinion for Application No. PCT/US2020/025655, mailed Jul. 22, 2020, 8 pages.

International Search Report and Written Opinion for Application No. PCT/US19/17646, mailed on Apr. 16, 2019, 11 pages.

International Search Report and Written Opinion for Application No. PCT/US2019/019501, mailed May 9, 2019, 8 pages.

International Search Report and Written Opinion for Application No. PCT/US2019/056979, mailed Dec. 18, 2019, 8 pages.

International Search Report and Written Opinion for Application No. PCT/US2019/062344, mailed Mar. 23, 2020, 17 pages.

International Search Report and Written Opinion for Application No. PCT/US2019/062768, mailed Mar. 9, 2020, 15 pages.

International Search Report and Written Opinion for Application No. PCT/US2019/064861, mailed Mar. 30, 2020, 18 pages.

International Search Report and Written Opinion for Application No. PCT/US2019/066513, mailed Apr. 21, 2020, 8 pages.

International Search Report and Written Opinion for Application No. PCT/US2019/066530, mailed Apr. 21, 2020, 8 pages.

International Search Report and Written Opinion for Application No. PCT/US2020/020672, mailed Jun. 29, 2020, 10 pages.

International Search Report and Written Opinion for Application No. PCT/US2021/012284, mailed May 6, 2021, 23 pages.

Partial European Search Report for Application No. EP19757451.0, mailed on Feb. 2, 2022, 12 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

International Search Report and Written Opinion for Application No. PCT/US2021/065544 mailed Jun. 2, 2022, 21 pages.

International Search Report and Written Opinion for Application No. PCT/US2021/065308, mailed Apr. 21, 2022. 13 pages.

(56) References Cited

OTHER PUBLICATIONS

Field Application Note—Journal Bearings, Retrieved from Wayback Machine URL: https://web.archive.org/web/20100110095051/http://www.reliabilitydirect.com/appnotes/jb.html, on Mar. 12, 2024, 04 pages.
International Search Report and Written Opinion for Application No. PCT/US2016/059527, mailed on Feb. 16, 2017, 13 pages.
Nicholson, C., et al., "Plane Bearings," ESC Report, BSA Educational Services Committee, Oct. 1994, vol. 5(1), 02 pages.

* cited by examiner

SURGICAL INSTRUMENTS FOR APPLYING MULTIPLE CLIPS

CROSS REFERENCE TO RELATED APPLICATIONS

This application is the National Stage of International Application No. PCT/US2021/012284 filed Jan. 6, 2021, which claims benefit of U.S. Provisional Application Ser. No. 62/958,195, filed Jan. 7, 2020, the entire disclosure of which is incorporated herein by reference for all purposes.

BACKGROUND

The field of the present disclosure relates to surgical instruments for dissecting, occluding and/or sealing tissue, and more particularly to surgical instruments capable of applying multiple rows of clips to tissue.

Minimally invasive medical techniques are intended to reduce the amount of extraneous tissue that is damaged during diagnostic or surgical procedures, thereby reducing patient recovery time, discomfort, and deleterious side effects. One effect of minimally invasive surgery, for example, is reduced post-operative hospital recovery times. The average hospital stay for a standard open surgery is typically significantly longer than the average stay for an analogous minimally invasive surgery (MIS). Thus, increased use of MIS could save millions of dollars in hospital costs each year. While many of the surgeries performed each year in the United States could potentially be performed in a minimally invasive manner, only a portion of the current surgeries uses these advantageous techniques due to limitations in minimally invasive surgical instruments and the additional surgical training involved in mastering them.

Improved surgical instruments such as tissue access, navigation, dissection and sealing instruments have enabled MIS to redefine the field of surgery. These instruments allow surgeries and diagnostic procedures to be performed with reduced trauma to the patient. A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, cautery tool, linear cutter, or needle holder.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console, which in turn control motion of the servo-mechanically operated slave instruments.

The servomechanism used for telesurgery will often accept input from two master controllers (one for each of the surgeon's hands) and may include two or more robotic arms on each of which a surgical instrument is mounted. Operative communication between master controllers and associated robotic arm and instrument assemblies is typically achieved through a control system. The control system typically includes at least one processor that relays input commands from the master controllers to the associated robotic arm and instrument assemblies and back from the instrument and arm assemblies to the associated master controllers in the case of, for example, force feedback or the like. One example of a robotic surgical system is the DA VINCI™ system commercialized by Intuitive Surgical, Inc. of Sunnyvale, California.

A variety of structural arrangements have been used to support the surgical instrument at the surgical site during robotic surgery. The driven linkage or "slave" is often called a robotic surgical manipulator, and exemplary linkage arrangements for use as a robotic surgical manipulator during minimally invasive robotic surgery are described in U.S. Pat. No. 7,594,912 (filed Sep. 30, 2004), U.S. Pat. No. 6,758,843 (filed Apr. 26, 2002), U.S. Pat. No. 6,246,200 (filed Aug. 3, 1999), and U.S. Pat. No. 5,800,423 (filed Jul. 20, 1995), the full disclosures of which are incorporated herein by reference in their entirety for all purposes. These linkages often manipulate an instrument holder to which an instrument having a shaft is mounted. Such a manipulator structure can include a parallelogram linkage portion that generates motion of the instrument holder that is limited to rotation about a pitch axis that intersects a remote center of manipulation located along the length of the instrument shaft. Such a manipulator structure can also include a yaw joint that generates motion of the instrument holder that is limited to rotation about a yaw axis that is perpendicular to the pitch axis and that also intersects the remote center of manipulation. By aligning the remote center of manipulation with the incision point to the internal surgical site (for example, with a trocar or cannula at an abdominal wall during laparoscopic surgery), an end effector of the surgical instrument can be positioned safely by moving the proximal end of the shaft using the manipulator linkage without imposing potentially hazardous forces against the abdominal wall. Alternative manipulator structures are described, for example, in U.S. Pat. No. 6,702,805 (filed Nov. 9, 2000), U.S. Pat. No. 6,676,669 (filed Jan. 16, 2002), U.S. Pat. No. 5,855,583 (filed Nov. 22, 1996), U.S. Pat. No. 5,808,665 (filed Sep. 9, 1996), U.S. Pat. No. 5,445,166 (filed Apr. 6, 1994), and U.S. Pat. No. 5,184,601 (filed Aug. 5, 1991), the full disclosures of which are incorporated herein by reference in their entirety for all purposes.

During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices. Manipulation and control of these end effectors is a particularly beneficial aspect of robotic surgical systems. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Endoscopic surgical clip appliers are used for a number of minimally invasive or endoscopic surgical procedures to occlude, ligate and/or seal vessels and tissue. Applying surgical clips usually involves compressing the clip over the surgical site, such as a blood vessel. Once applied to the vessel, the compressed surgical clip terminates the flow of fluid therethrough.

Conventional surgical clips are designed to be compressed into a latched or locked position around a grasped vessel or other grasped tissue. Typically, the surgical instrument includes jaws that can be closed to engage bosses formed on the clips. These bosses are forced inwardly about a hinge section causing the first and second legs of the clip being applied to close around the grasped vessel. The tip section of the second leg then begins to contact a hook section. Upon opening of the jaws, the tip section snaps into and is conformably seated in the latching recess, at which point the clip is secured into a latched condition.

Conventional endoscopic surgical clip appliers include a surgical instrument having an end effector with movable jaws and a clip cartridge that is installed within the end effector. The clip cartridge typically contains a single row of clips Constraints on overall instrument size, however, limit the number of clips contained in the clip cartridge. Typically, one row of clips may include about 2 to 6 clips. Once the entire row of clips has been discharged and applied to tissue, the surgeon must remove the surgical instrument from the cannula and manually reload a new cartridge into the instrument. This may disrupt the workflow of the procedure and result in unnecessary delays.

Accordingly, while the new telesurgical systems and devices have proven highly effective and advantageous, still further improvements would be desirable. In generally, it would be desirable to provide improved surgical instruments that are capable of discharging multiple rows of clips per single instrument insertion within the patient. Additionally, it would be advantageous to provide improved surgical instruments that accommodate multiple rows of clips without sacrificing the overall instrument size, thereby allowing for the design of compact and maneuverable instruments.

SUMMARY

The following presents a simplified summary of the claimed subject matter in order to provide a basic understanding of some aspects of the claimed subject matter. This summary is not an extensive overview of the claimed subject matter. It is intended to neither identify key or critical elements of the claimed subject matter nor delineate the scope of the claimed subject matter. Its sole purpose is to present some concepts of the claimed subject matter in a simplified form as a prelude to the more detailed description that is presented later.

In one aspect of the invention, a surgical instrument for applying surgical clips to tissue comprises an end effector having first and second jaws that are movable between open and closed positions and configured to receive at least first and second rows of clips in the open position. The instrument further includes an actuator coupled to the end effector and configured to move the jaws into the closed position and to drive the first and second rows of clips into tissue. This allows an operator to apply multiple rows of clips to tissue with a single instrument insertion, which obviates the need to remove the surgical instrument from the cannula to manually reload a new cartridge, thereby reducing the overall time of the surgical procedure.

In certain embodiments, the actuator comprises a drive element coupled to a pusher. The drive element is configured to open and close the jaws of the end effector. The pusher is configured to engage and sequentially form the first and second rows of clips as the jaws are closed on the tissue.

In one such embodiment, the first row of clips is disposed within the instrument laterally to the second row of clips relative to a longitudinal axis of the end effector. The actuator is configured to move the pusher laterally during translation of the drive element through the end effector. This allows the pusher to be moved laterally from one row of clips to the other, enabling the instrument to apply at least two rows of clips in a single instrument insertion.

The actuator may be configured to translate the drive element distally such that the pusher engages the first row of clips. Once the first row of clips is completely discharged, the actuator may be configured to retract the pusher proximally such that the pusher is also shifted laterally such that it is aligned with the second row of clips in the cartridge. The actuator may then translate the drive element distally to engage the second row of clips. The actuator may also be configured to close the jaws when the drive element is translated distally and to open the jaws when the drive element is translated proximally. This allows another clip to be advanced into the open jaws. The drive element may further include one or more linkages coupled to one of the first and second jaws, wherein the linkages are configured to close the jaws as the drive element is translated distally and to open the jaws as the drive element is translated proximally.

In certain embodiments, the pusher is biased towards the first row of clips upon installation of a clip cartridge. The end effector may further include a biasing surface, such as a spring, ramp or the like, configured to laterally translate the pusher towards the second row of clips as the pusher is retracted proximally by the drive element. The biasing surface may include a cutout that extends in a lateral direction for receiving the drive element. The drive element may comprise a flexible rod or cable extending through the cutout and configured for lateral movement through the cutout. This allows the drive element to shift from one row of clips to another.

In another aspect, the surgical instrument further comprises a clip cartridge configured for positioning between the first and second jaws. The clip cartridge includes at least two rows of clips that may be oriented parallel to the longitudinal axis of the instrument. The clip cartridge may include an inclined surface configured to laterally displace the pusher to align the pusher with one of the rows of clips.

In certain embodiments, the actuator is configured for coupling to a robotic teleoperated control system. The robotic teleoperated control system may comprise one or more manipulator arms coupled to the actuator and configured to translate the drive element proximally and distally relative to the end effector. For example, in one configuration, the actuator will be manipulated by the robotic manipulator assembly to move the jaws of the end effector between an open position and a closed position. In the closed position, the jaws are actuated into compressing contact with the legs of a clip, thereby compressing the clip into a latched or locked position around a vessel or other tissue In another aspect, a surgical instrument comprises an end effector having a channel for receiving a cartridge and including first and second jaws movable between open and closed positions. The instrument further comprises a drive member coupled to the end effector and configured to translate along a longitudinal axis of the end effector to move the jaws between the open and closed positions. The drive member is configured to displace laterally relative to a longitudinal axis of the end effector to engage the cartridge at first and second, laterally spaced, positions on the cartridge. This allows the instrument to actuate multiple rows of fasteners, such as clips, staples or the like, within the cartridge, thereby reducing the need to replace cartridges during a surgical procedure.

The drive member may be moved laterally as the drive member moves along the longitudinal axis. In one aspect, the actuator is configured to translate the drive member distally such that the drive member engages the cartridge at the first position, retract the drive member proximally and then translate the drive member distally to engage the cartridge at the second position. The actuator may be configured to close the jaws when the drive element is translated distally and to open the jaws when the drive element is translated proximally.

In certain embodiments, the instrument further comprises an actuator configured to translate the drive member along the longitudinal axis. The actuator may be configured for coupling to a robotic teleoperated control system. The robotic teleoperated control system may comprise one or more manipulator arms coupled to the actuator and configured to translate the drive element proximally and distally relative to the end effector.

In another aspect, a clip cartridge for use with a surgical instrument comprises a housing including a first channel configured to receive a first row of clips and a second channel configured to receive a second row of clips. The first channel is disposed laterally of the second channel relative to a longitudinal axis of the housing. The channels may be separated by a central wall within the housing. The cartridge further includes an inclined surface extending proximally from the housing and configured to engage and urge a drive element of the surgical instrument into alignment with the first channel upon installation of the clip cartridge into the surgical instrument.

In certain embodiments, the first and second channels comprises a proximal opening for receiving the drive element of the surgical instrument. The inclined surface may comprise a tab extending transversely to the longitudinal axis of the housing between the two channels to urge or guide the drive member to one of the channels.

In certain embodiments, the housing may further include one or more projections extending from the housing. The projections are configured to engage with cutouts within the surgical instrument to secure the cartridge to the surgical instrument. The housing may further include tapered sides on a proximal end portion of the clip cartridge. The tapered sides allow the cartridge to take up less space in the surgical instrument to provide additional functionality in the instrument. For example, the tapered sides may provide room for linkages or other drive elements that extend past the clip cartridge to actuate the jaws of the instrument and/or engage the clips in the cartridge.

It is to be understood that both the foregoing general description and the following detailed description are exemplary and explanatory only and are not restrictive of the disclosure. Additional features of the disclosure will be set forth in part in the description which follows or may be learned by practice of the disclosure

BRIEF DESCRIPTION OF THE DRAWINGS

The above and other aspects, features, and advantages of the present surgical instruments will become more apparent in light of the following detailed description when taken in conjunction with the accompanying drawings in which.

DETAILED DESCRIPTION

Figure 1:
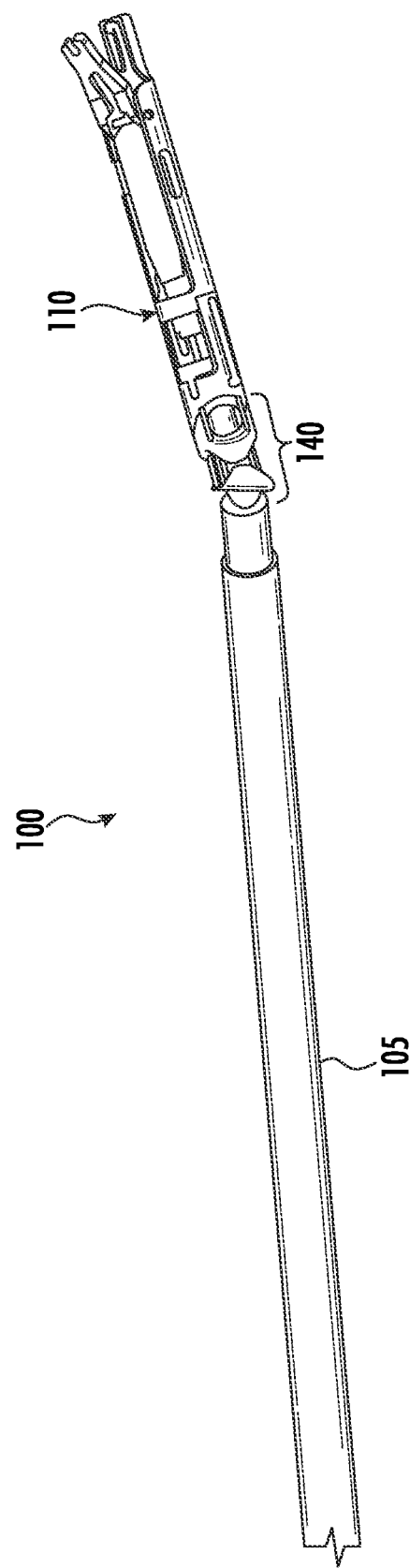
FIG. 1 is a perspective view of a surgical instrument in accordance with an illustrative embodiment of this disclosure.

Particular embodiments of the present surgical instruments are described hereinbelow with reference to the accompanying drawings; however, it is to be understood that the disclosed embodiments are merely exemplary of the disclosure and may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure. Well-known functions or constructions are not described in detail to avoid obscuring the present disclosure in any unnecessary detail. Like numbers in two or more figures represent the same or similar elements. Furthermore, elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment. Moreover, the depictions herein are for illustrative purposes only and do not necessarily reflect the actual shape, size, or dimensions of the system or illustrated components.

Surgical instruments of the present disclosure are adapted to be used with a robotic system for applying ligating clips. The surgical instruments will generally include an actuation mechanism that controls the orientation and movement of the end effector. The actuation mechanism will typically be controlled by a robotic manipulator assembly that is controlled remotely by a user. For example, in one configuration, the actuation mechanism will be manipulated by the robotic manipulator assembly to move the jaws of the end effector between an open position and a closed position. In the closed position, the jaws are actuated into compressing contact with the legs of a clip, thereby compressing the clip into a latched or locked position around a vessel or other tissue While the following disclosure is presented with respect to surgical instruments that are compatible with surgical clip cartridges, it should be understood that certain features of the presently described surgical instruments may be readily adapted for use in any type of surgical clamping, cutting, ligating, dissecting, clipping, cauterizing, suturing and/or sealing instrument, whether or not the surgical instrument applies a fastener. For example, the presently described drive member and actuation mechanism may be employed in an electrosurgical instrument wherein the jaws include electrodes for applying energy to tissue to treat (e.g., cauterize, ablate, fuse, or cut) the tissue. In addition, the features of the presently described surgical instruments may be readily adapted for may be readily adapted for use in other types of cartridges, such as linear and/or purse string stapler cartridges. Additionally, the features of the presently described surgical stapling instruments may be readily adapted for use in surgical instruments that are activated using any technique within the purview of those skilled in the art, such as, for example, manually activated surgical instruments, powered surgical instruments (e.g., electro-mechanically powered instruments), robotic surgical instruments, and the like.

The embodiments of the present disclosure may also be incorporated into a variety of different surgical instruments, such as those described in commonly-assigned, co-pending U.S. patent application Ser. Nos. 16/205,128, 16/427,427, 16/678,405, 16/904,482, 17/081,088 and 17/084,981 and International Patent Nos. PCT/US2019/107646, PCT/US2019/019501, PCT/US2019/062344, PCT/US2020/54568, PCT/US2019/064861, PCT/US2019/062768, PCT/2020/025655, PCT/US2020/056979, PCT/2019/066513, PCT/US2020/020672, PCT/US2019/066530 and PCT/US2020/033481, the complete disclosures of which are incorporated by reference herein in their entirety for all purposes as if copied and pasted herein.

FIG. 1 shows the distal end portion of a surgical instrument 100 in accordance with an illustrative embodiment of the present disclosure. Surgical instrument 100 includes an end effector 110, an articulation mechanism 140, and an elongated shaft 105. The proximal end portion of elongate shaft 105 is operatively connected to an actuation mechanism (not shown), although as those skilled in the art reading this disclosure will appreciate, components of the actuation mechanism may extend into, and/or pass through elongated shaft 105 and/or articulation mechanism 140.

Surgical instrument 100 will further include a backend mechanism (not shown) coupled to the proximal end portion of elongate shaft 105. The backend mechanism typically provides a mechanical coupling between the drive tendons or cables of the instrument and motorized axes of the mechanical interface of a drive system (see, for example, element 510 in FIG. 10 discussed in more detail below). Further details of known backend mechanisms and surgical systems are described, for example, in U.S. Pat. Nos. 8,597,280, 7,048,745, and 10,016,244. Each of these patents is hereby incorporated by reference in its entirety.

Actuation mechanisms of surgical instrument 100 employ drive cables that are used in conjunction with a system of motors and pulleys. Powered surgical systems, including robotic surgical systems that utilize drive cables connected to a system of motors and pulleys for various functions including opening and closing of jaws, as well as for movement and actuation of end effectors are well known. Further details of known drive cable surgical systems are described, for example, in U.S. Pat. Nos. 7,666,191 and 9,050,119 both of which are hereby incorporated by reference in their entireties.

Figure 2:
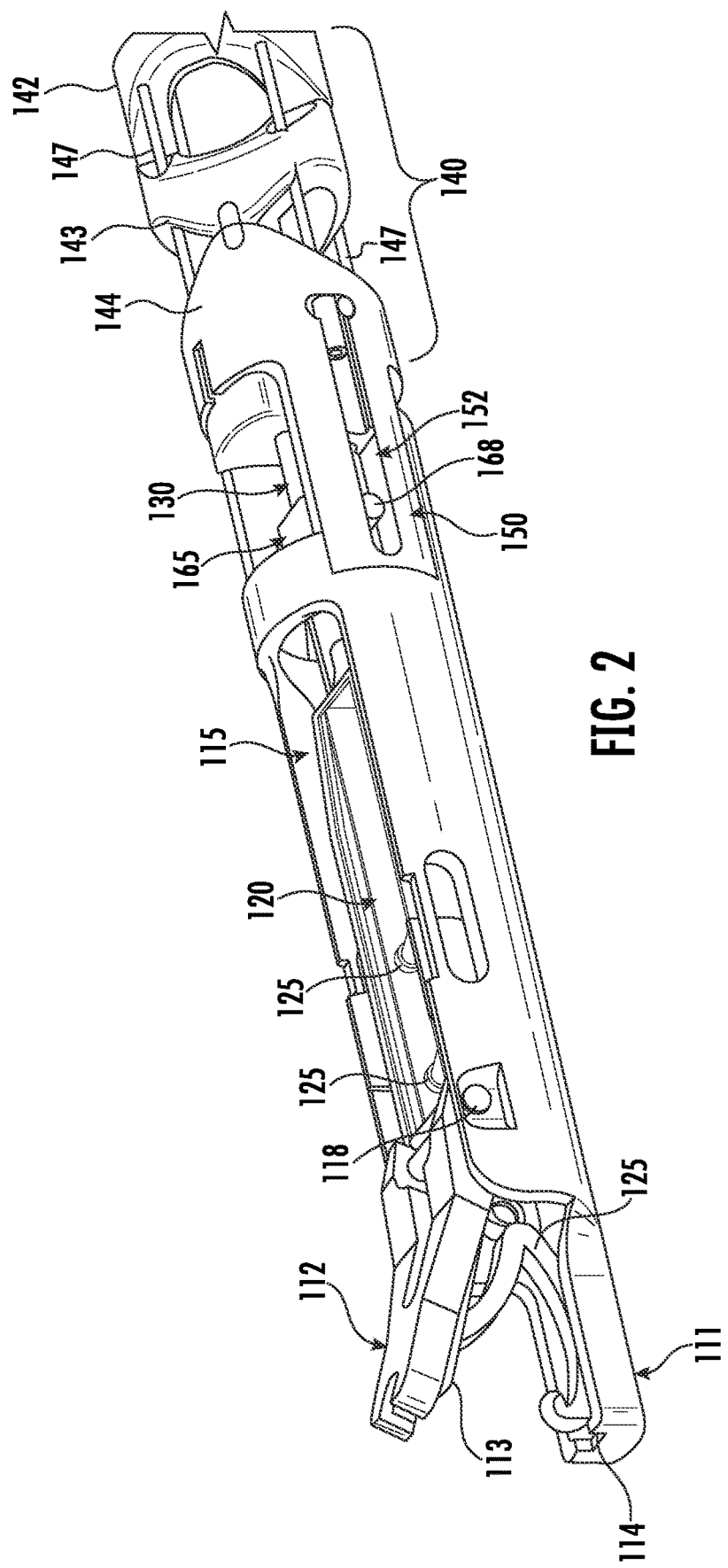
FIG. 2 is a perspective view of the distal end portion of the surgical instrument of FIG. 1 including the end effector and a portion of an articulation mechanism.

With reference now to FIG. 2, end effector 110 includes a first jaw 111, a second jaw 112, a channel 115, a cartridge 120, an actuation mechanism 130, an articulation mechanism 140, and a clevis 150. Jaws 111, 112 are configured to move between an open position (as shown in FIG. 2) where the jaws are spaced apart from one another and a closed position to force the jaws into compressing contact with the legs of an unformed clip to close (and form) the clip around tissue to be ligated. In certain embodiments, second jaw 112 is a movable jaw configured to move from an open position to a closed position relative to first jaw 111. In other embodiments, first jaw 111 is a movable jaw configured to move between open and closed positions relative to second jaw 112. In still other embodiments, both jaws 111, 112 are movable relative to each other.

Jaws 111, 112 further include an upper guide track 113 and a lower guide track 114. Guide tracks 113,114 are designed to allow jaws 111, 112 to easily grip a distal-most unformed clip, and to maintain alignment of the distal-most clip throughout actuation of surgical instrument 100. Channel 115 of end effector 110 is configured to receive a cartridge 120 containing at least two rows of clips 125. Clips 125 are generally in an unformed configuration within the cartridge. On the proximal side of end effector 110, clevis 150 connects channel 115 of end effector 110 and articulation mechanism 140 (e.g., a wrist assembly 140) with shaft 105.

Wrist assembly 140 is positioned between clevis 150 and elongated shaft 105. Wrist assembly 140 may provide a desired amount of motion, such as +/−90 degrees in a pitch or yaw direction. In embodiments, wrist assembly 140 may include a proximal link 142, a middle link 143, and a distal link 144 that collectively determine the kinematic pitch and yaw motion of the wrist assembly 140. As shown, the interface between the proximal link 142 and the middle link 143 defines a joint that determines yaw movement of wrist assembly 140. The interface between the distal link 144 and the middle link 143 defines a joint that determines pitch movement of wrist assembly 140. However, in an alternative embodiment of a wrist assembly, this relationship can be reversed such that wrist assembly 140 pitches between proximal link 142 and middle link 143 and yaws between distal link 144 and middle link 143. Cables 147 are drivingly coupled with the wrist assembly 140 and actuated to impart motion to wrist assembly 140. Differential movement of cables 147 can be used to actuate wrist assembly 140 to pitch and yaw at various angles. Additional details of articulation mechanisms usable with the embodiments disclosed herein are disclosed in Int'l. Pub. No. WO 2015/127250A1 and U.S. Publication No. 2017/0215977 A1, the entire disclosure of each of which is incorporated by reference herein.

Movement of jaws 111, 112 between the open and closed position is achieved by an actuation mechanism which is operatively coupled with a power source configured to power a series of motors and pulleys to push or pull one or more drive elements coupled with various components of end effector 110. In such a "push/pull" design, a compression/tension element may be used to move the end effector components. Pulling (tension) is used to move the component in one direction, and pushing (compression) is used to move the component in the opposite direction. Surgical instruments in accordance with this disclosure may employ drive cables that are used in conjunction with a system of motors and pulleys to push or pull the drive element. Powered surgical systems, including robotic surgical systems that utilize drive cables connected to a system of motors and pulleys for various functions including opening and closing of jaws, as well as for movement and actuation of end effectors are well known. Further details of known drive cable surgical systems are described, for example, in U.S. Pat. Nos. 7,666,191 and 9,050,119 both of which are hereby incorporated herein by reference in their entireties.

The length of a slot 152 formed in clevis 150 defines the length of the gripping/actuation motion of a given surgical instrument. Cam pin 168 is operatively coupled to a drive element 165, and rides through slot 152 upon actuation, transitioning jaws 111, 112 between the open and closed positions as a series of cooperating arm linkages generate the force needed to move jaws 111, 112. In certain embodiments, an upper cam pin 118 is pulled in the proximal direction to pivot jaws 111, 112 towards the closed position to compress the distal-most clip. The mechanism by which jaws 111, 112 are closed will be described in further detail below (See FIG. 8).

Figure 3:
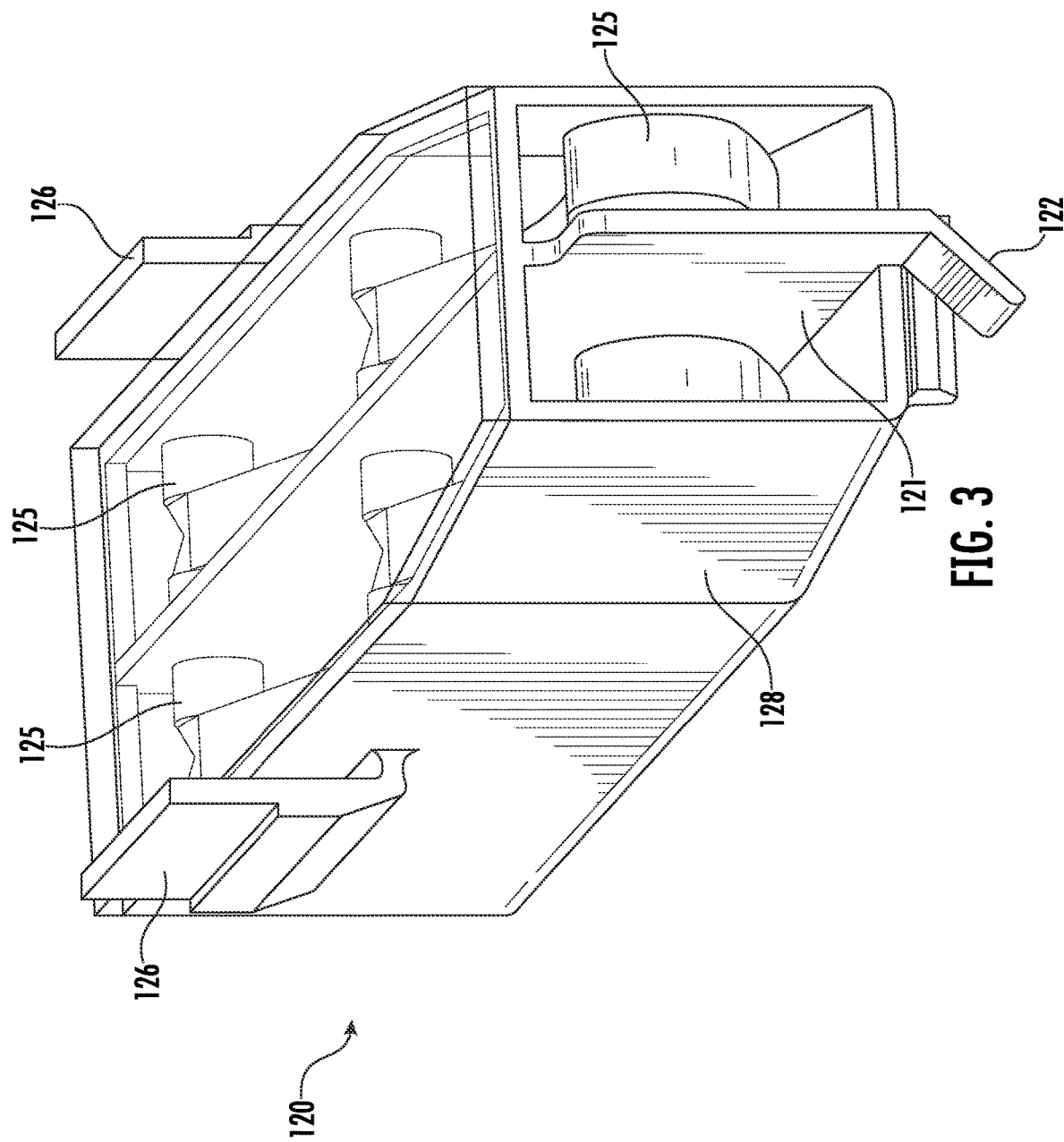
FIG. 3 is a rear perspective view of a cartridge compatible with the surgical instrument of FIG. 1 including two rows of clips.
Figure 3A:
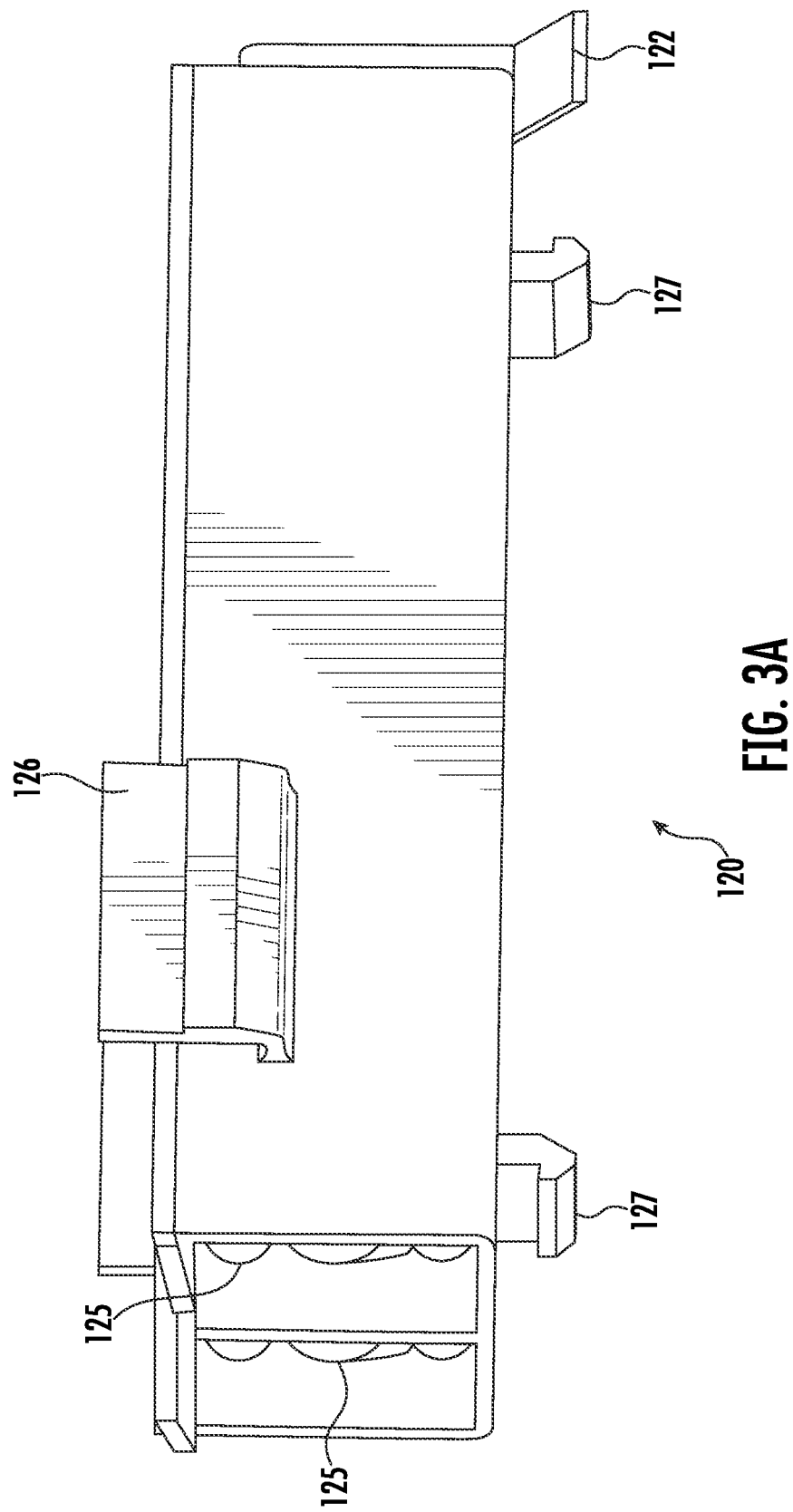
FIG. 3A is a perspective side view of the cartridge of FIG. 3.

FIGS. 3 and 3A illustrate a cartridge 120 that may be installed into surgical instrument 100 according to the present disclosure. In certain embodiments, cartridge 120 includes a central wall 121 separating a first and second row of clips 125. Of course, it will be recognized that cartridge 120 may be adapted to accommodate more than two rows of clips, such as three, four or more rows. Typically, each row of clips may contain 1 to 6 clips, preferably about 2 to 6 clips. Thus, the overall cartridge in FIGS. 3 and 3A may contain between about 2 to 12 clips. Cartridge 120 may be constructed from any suitable materials known in the art, such as a single-molded plastic body. Cartridge 120 may be adapted to accommodate any suitable desired sizes of clips 125. In an exemplary embodiment, cartridge 120 can be adapted to accommodate any size of HEM-O-LOK® clips commercially available.

Cartridge 120 may include locking features formed thereon including upper fins 126 and lower fins 127 configured to engage cutouts 116 (best seen in FIG. 4) formed on channel 115 of end effector 110. In embodiments, cartridge 120 may include tapered sides 128 to provide more space within end effector 110 of instrument 100. For example, tapered sides 128 may be formed on the proximal end of cartridge to allow for more room for arm linkages 170 to accommodate the high forces required for actuation of clips 125 (see FIG. 8).

Cartridge 120 further includes an inclined surface, such as proximal tab 122 for biasing the drive element of surgical instrument 100 towards one of the rows of clips. Proximal tab 122 is configured to, upon installation, direct a pusher 131 of drive element 165 towards a first side of cartridge 120 containing a first row of clips 125. Of course, it will be recognized that the inclined surface of tab 122 could be reversed such that pusher 131 is initially directed towards the second row of clips 125. Alternatively, end effector 110 of instrument 100 may comprise a biased surface to direct pusher 131 to one of the rows of clips, or pusher 131 may be designed such that it is automatically aligned with one of the rows of clips upon installation of cartridge 120.

Figure 4:
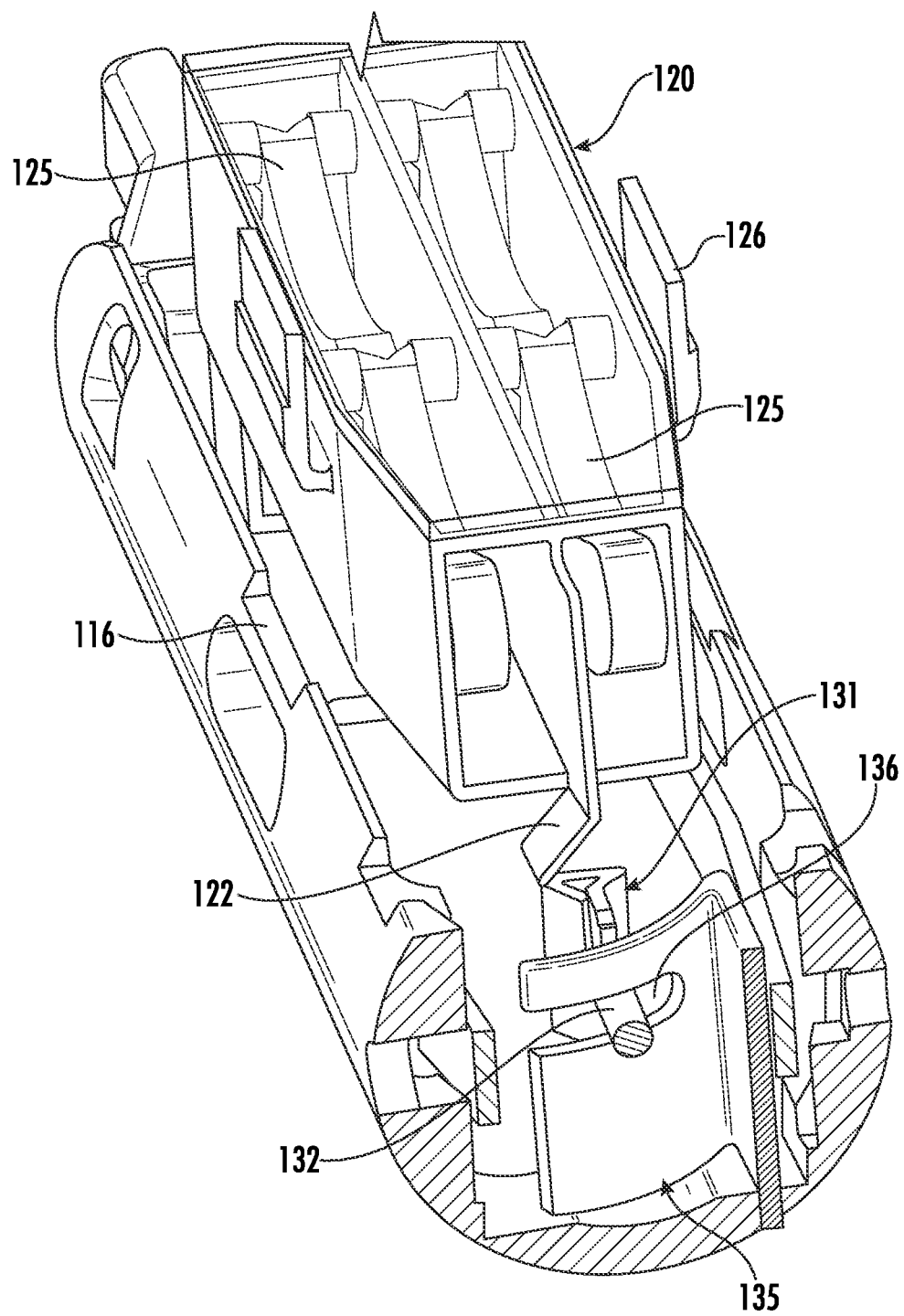
FIG. 4 is a rear perspective view of an illustrative cartridge being installed into a portion of the end effector of the surgical of FIG. 1.
Figure 5:
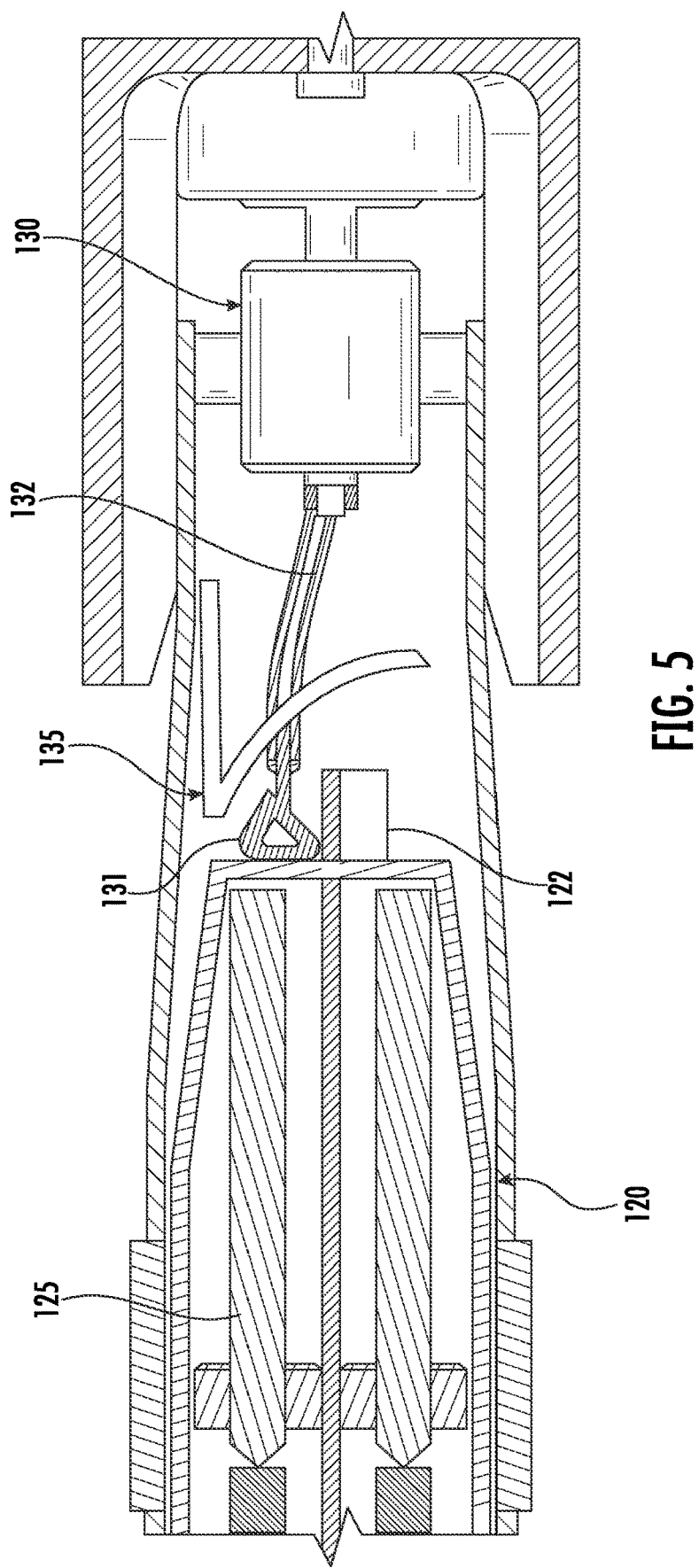
FIG. 5 is a top-down view with parts removed of the end effector of the surgical instrument of FIG. 1 having an unfired cartridge installed and a pusher positioned on a first side of the cartridge to fire a first row of clips.

In FIGS. 4 and 5, the exemplary cartridge 120 of FIGS. 3 and 3A is shown being installed into a channel 115 of end effector 110. As cartridge 120 is installed, proximal tab 122 directs a pusher 131 to a first side of channel 115 such that it is aligned with a first row of clips 125, and upon actuation, may drive clips 125 distally towards jaws 111, 112. A drive cable 132 is attached to the proximal end of pusher 131 and passes through a lateral cutout 136 in a spring 135. As shown in FIG. 4, cutout 136 may have a length substantially similar to the width of cartridge 120 to allow for drive cable 132 to move along cutout 136 as needed to align pusher 131 with a given row of clips. To facilitate the movement of drive cable 132 along cutout 136, drive cable 132 may be flexible as best seen in FIG. 5.

In an alternative embodiment, end effector 110 may be designed to receive two or more clip cartridges that each contain a single row of clips. In this embodiment, the end effector 110 may have one or more central walls (similar to central wall 121) that are integrated into channel 115 to allow for multiple clip cartridges to be installed therein.

Figure 8:
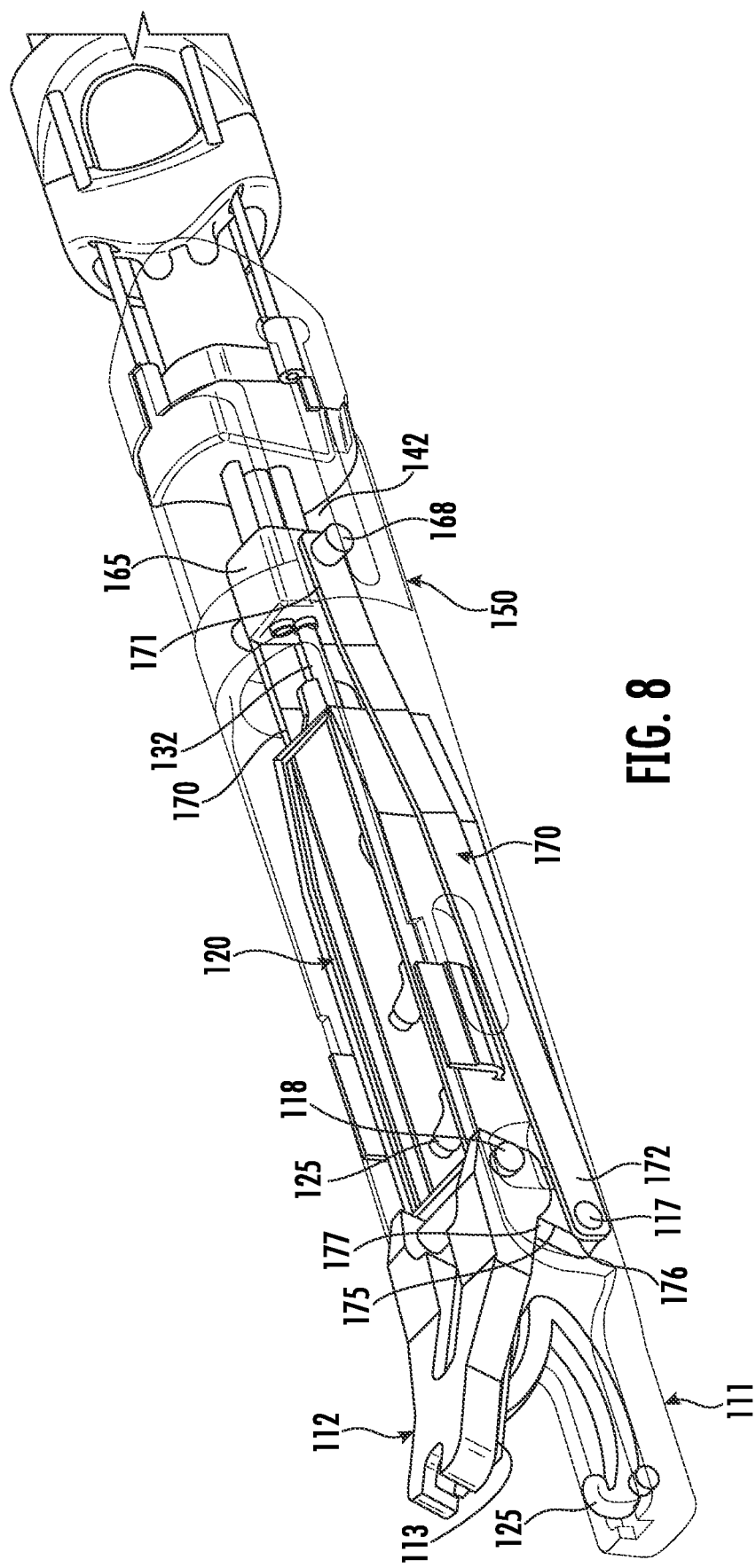
FIG. 8 is a perspective side view with parts removed of a jaw closing mechanism in accordance with an embodiment of the present disclosure.

Drive cable 132 may pass through a substantially central portion of a drive element 165 (see FIG. 8). Once pusher 131 is aligned with the first row of clips within cartridge 120, a user may then advance each clip within the first row of unformed clips to a position between jaws 111, 112 for formation about a vessel until that row of clips has been exhausted. In embodiments, a series of tracks, channels, or other similar structures may function to align the distal-most unformed clip with guide tracks 113 of jaws 111,112 as the distal-most unformed clip is driven distally past cartridge 120 towards jaws 111,112. The distal end of drive cable 132 may be welded to the proximal end of pusher 131 to provide a smooth interface between the components as drive cable 132 is pushed and pulled by the actuation mechanism. Similar drive mechanisms in which a drive cable is instead coupled to a cutting element are described, for e.g., in U.S. Pat. No. 9,055,961, the entire disclosure of each of which is incorporated herein by reference.

Figure 6:
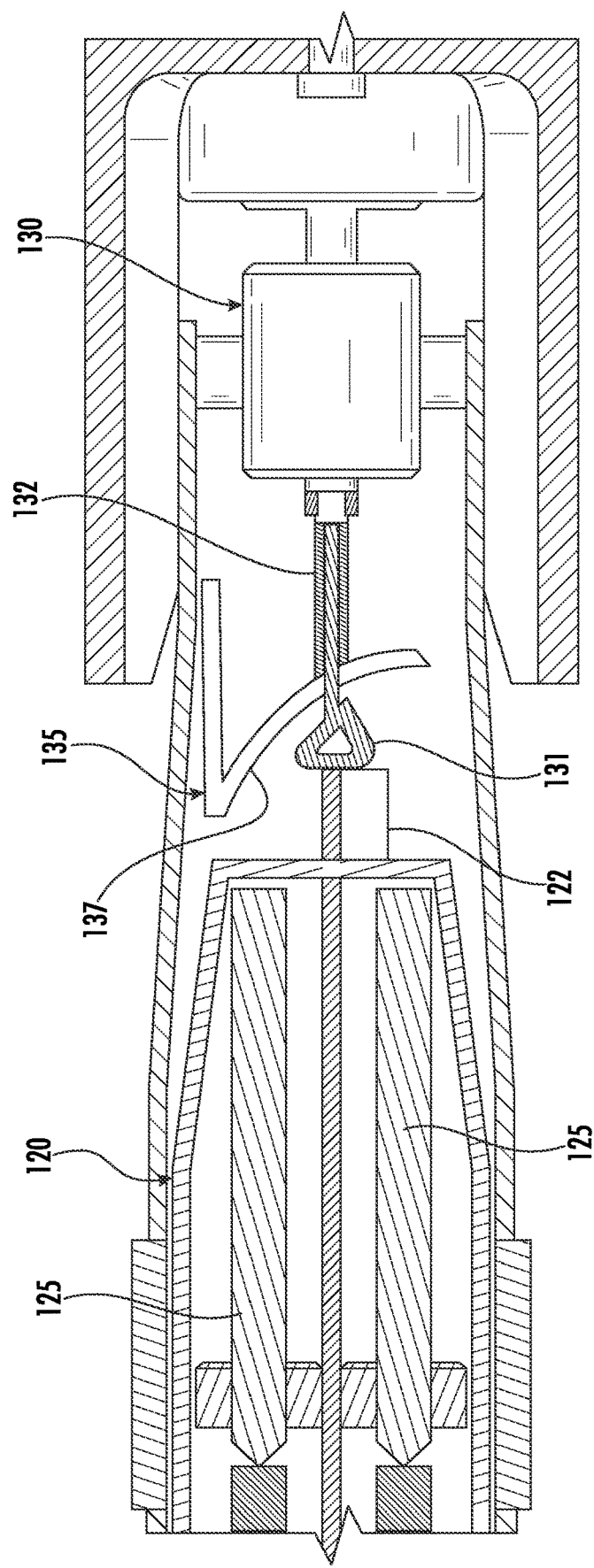
FIG. 6 is a top-down view with parts removed illustrating retraction of a pusher through the end effector of the surgical instrument of FIG. 1.
Figure 7:
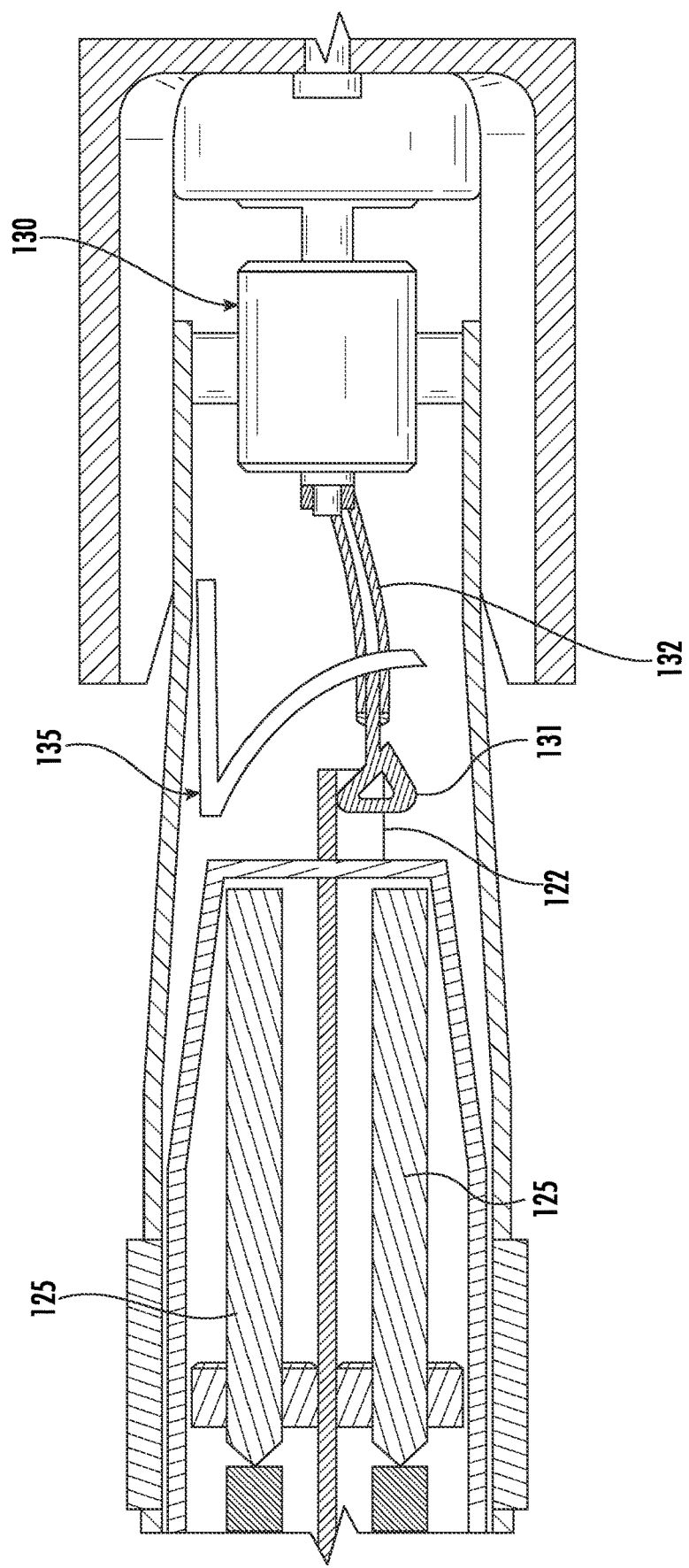
FIG. 7 is a top-down view with parts removed of the end effector of the surgical instrument of FIG. 1 having a pusher positioned on a second side of the cartridge to drive a second row of clips.

In FIGS. 6 and 7, the first row of clips has been completely fired or discharged, and the mechanism by which a user may switch from the first row of clips to a second row of clips is shown. In FIG. 6, an actuation mechanism is pulling drive cable 132 proximally thereby causing retraction of pusher 131. When retracted, pusher 131 contacts a distal surface 137 of spring 135. Distal surface 137 of spring 135 is curved such that, upon retraction, pusher 131 rides along distal surface 137 urging pusher 131 towards the second row of clips. When retraction of pusher 131 has been completed, pusher 131 is able to clear proximal tab 122 of cartridge 120, and is urged into alignment with the second row of clips within cartridge 120. In FIG. 7, pusher 131 is shown in alignment with the second row of clips within cartridge 120. The second row of clips may then be fired using the previously described actuation mechanism from the surgical instrument until the second row of clips is exhausted. Clips 125 may be advanced into jaws 111, 112 by any means known to those skilled in the art.

Of course, it will be recognized by those of skill in the art that pusher 131 may be moved laterally from one row of clips to another through a variety of different mechanisms. For example, instrument 100 may include a separate actuator (not shown) that laterally displaces pusher 131 such that spring 135 and/or tab 122 are not required. In this embodiment, pusher 131 may be designed such that it is initially aligned with one of the rows of clips. An actuator may displace pusher 131 to the other row of clips either while the pusher is being translated longitudinally, or as a separate and independent movement. The actuator may be either controlled by the operator, or it may function automatically when the first row of clips has been fully discharged.

Figure 8A:
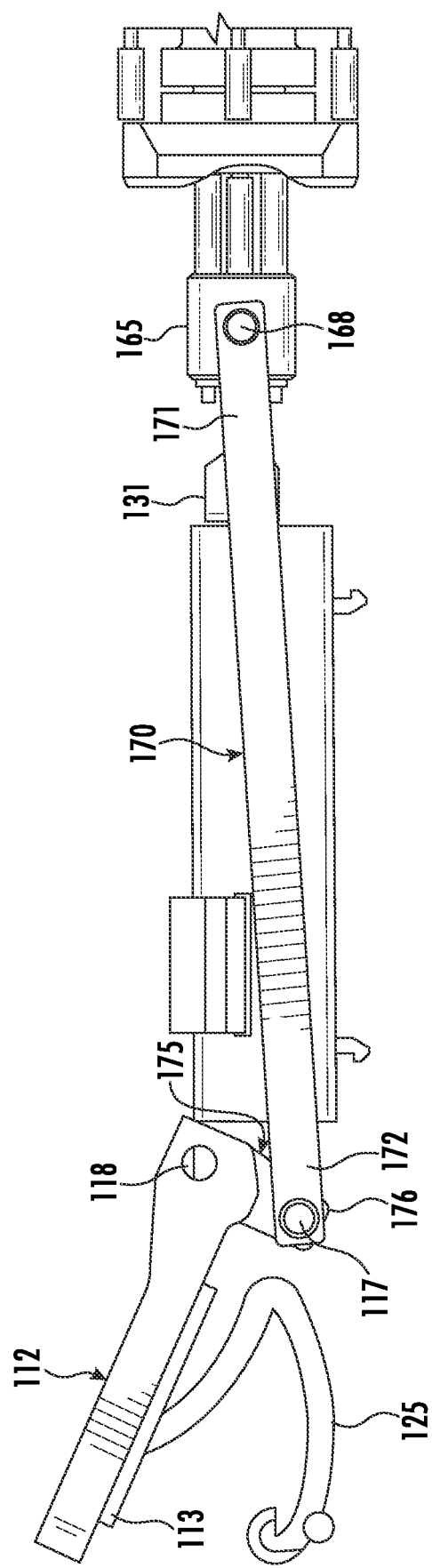
FIG. 8A is a side view with parts removed of a jaw closing mechanism in accordance with an embodiment of the present disclosure.

FIGS. 8 and 8A illustrate an exemplary jaw-closing mechanism used with a surgical instrument in accordance with the present disclosure. In FIG. 8, movable jaw 112 is shown with a clip 125 contained within upper guide track 113. A drive element 165, operatively connected to actuation mechanism 130, includes a pair of pins 168 configured to ride through a slot 142 in clevis 150 upon pushing or pulling of drive element 165. In embodiments, a series of drive cables may be operatively connected to drive element 165 to actuate motion of drive element 165. Drive element 165 is also coupled with a first pair of arm linkages 170. Proximal ends 171 of arm linkages 170 are coupled to pins 168, thereby coupling the first pair of arm linkages 170 to drive element 165. The distal ends 172 of arm linkages 170 are secured to a lower pin 117 positioned between stationary jaw 1111 and a distal end 124 of cartridge 120. A second pair of arm linkages 175 connects first pair of arm linkages 170 to movable jaw 112. As shown in FIG. 8, a lower portion 176 of arm linkages 175 is secured to lower pin 117, while upper portion 177 of arm linkages 175 is secured to an upper pin 118. Movable jaw 112 is also secured to and coupled with upper pin 118.

To effect closing of jaws 111, 112 and to compress clip 125, drive element 165 is pulled in the proximal direction through the use of drive cables or other suitable mechanisms within the purview of those skilled in the art. As drive element 165 is pulled proximally, first and second arm linkages 170, 175 cooperate to generate sufficient force to form clips 125 around tissue grasped between jaws 111, 112.

In the practice of ligating a vessel as understood by persons skilled in the art, surgical clips are designed to be compressed into a latched or locked position around a grasped vessel or other grasped tissue. Typically, the jaws of a surgical instrument for applying clips, such as the surgical instrument described in the present disclosure, engage bosses formed on the clips. These bosses are forced inwardly about a hinge section causing the first and second legs of the clip being applied to close around the grasped vessel, with a convex inner surface of the second leg and a complementary concave inner surface of the first leg contacting the outer wall of the vessel. The tip section of the second leg then begins to contact a hook section. Further pivotal movement of the jaws of the surgical instrument longitudinally elongates the first leg and deflects the hook section outwardly, allowing the tip section to align with and engage a latching recess. Upon opening of the jaws, the tip section snaps into and is conformably seated in the latching recess, at which point the clip is secured into a latched condition. In the latched condition, the tip section is engaged between the concave inner surface of the first leg and a beveled surface of the hook section, thereby securely clamping a designated vessel or other tissue between the concave inner surface of the first leg and convex inner surface of the second leg. For additional details on the formation of clips by surgical instruments for applying clips see, e U.S. Pat. No. 7,211,092, the entire disclosure of which is incorporated herein by reference.

Figure 9A:
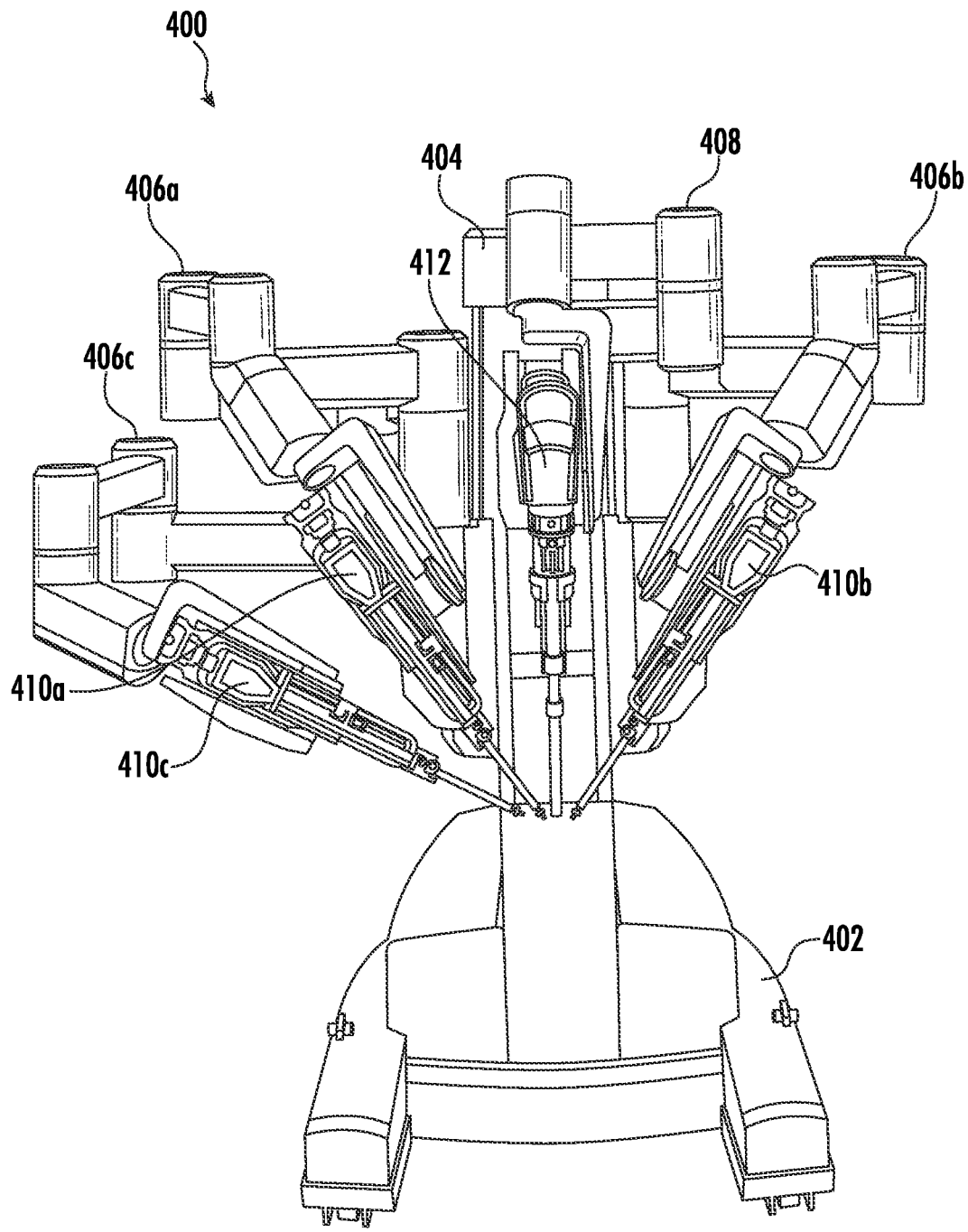
FIG. 9A is a front elevation, diagrammatic view of an exemplary patient side cart of a teleoperated surgical system.

As noted above, the present surgical instruments may be employed in a robotic teleoperated surgical system. FIG. 9A is a front elevation view of an exemplary embodiment of a patient side cart 400 of a teleoperated surgical system. The patient side cart 400 includes a base 402 that rests on the floor, a support tower 404 mounted on the base 402, and one or more manipulator arms mounted on the support tower 404 and that support surgical instruments and/or vision instruments (e.g., a stereoscopic endoscope). As shown in FIG. 9A, manipulator arms 406 a, 406 b are arms that support, and transmit forces to manipulate, the surgical instruments used to grasp and move tissue, and arm 408 is a camera arm that supports and moves the endoscope. FIG. 9A also shows a third manipulator arm 406 c that is supported on the back side of support tower 404 and that is positionable to either the left or right side of the patient side cart as desired to conduct a surgical procedure.

Interchangeable surgical instruments 410 a, 410 b, 410 c can be installed on the manipulator arms 406 a, 406 b, 406 c, and an endoscope 412 can be installed on the camera arm 108. Those of ordinary skill in the art reading this disclosure will appreciate that the arms that support the instruments and the camera may also be supported by a base platform (fixed or moveable) mounted to a ceiling or wall, or in some instances to another piece of equipment in the operating room (e.g., the operating table). Likewise, they will appreciate that two or more separate bases may be used (e.g., one base supporting each arm).

Control of the robotic surgical system, including control of the surgical instruments, may be effectuated in a variety of ways, depending on the degree of control desired, the size of the surgical assembly, and other factors. In some embodiments, the control system includes one or more manually operated input devices, such as a joystick, an exoskeletal glove, pincher or grasper assemblies, buttons, pedals, or the like. These input devices control servo motors which, in turn, control the articulation of the surgical assembly. The forces generated by the servo motors are transferred via drivetrain mechanisms, which transmit the forces from the servo motors generated outside the patient's body through an intermediate portion of the elongate surgical instrument 110 to a portion of the surgical instrument inside the patient's body distal from the servo motor.

Figure 9B:
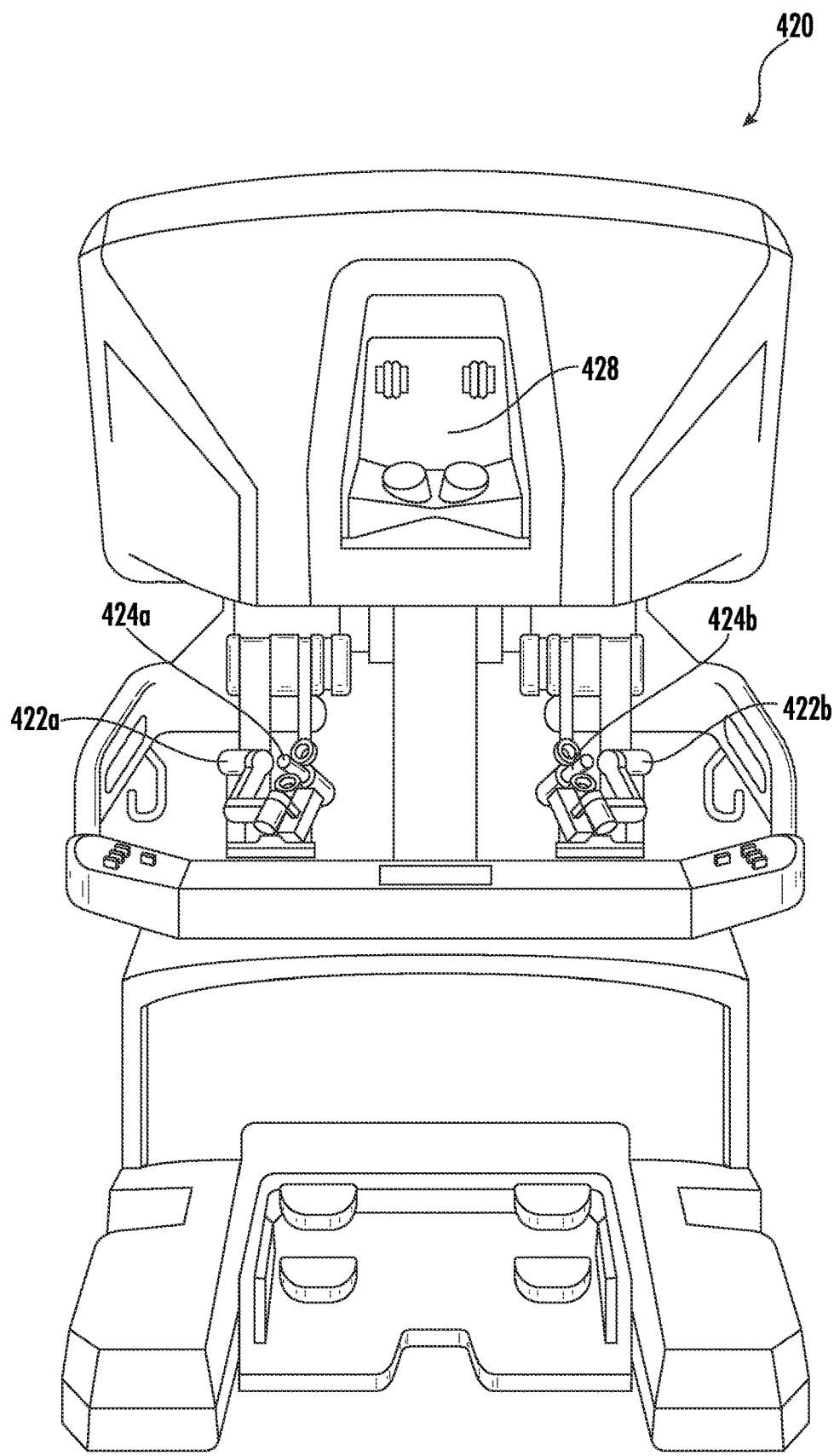
FIG. 9B is a front elevation, diagrammatic view of an exemplary surgeon's console of a teleoperated surgical system.

FIG. 9B is a front elevation view of an exemplary surgeon's console 420 of a teleoperated surgical system for controlling the insertion and articulation of surgical instruments 410. The surgeon or other system operator manipulates input devices by moving and repositioning input devices within console 420. As illustrated in the exemplary embodiment of FIG. 9B, the surgeon's console is equipped with master controllers or master input devices. As illustrated in FIG. 9B, master input devices may include left and right multiple degree-of-freedom (DOF) master tool manipulators (MTM's) 422 a, 422 b, which are kinematic chains that are used to control the surgical tools (which include the endoscope and various cannulas mounted on arms 406, 408 of the patient side cart 400). Each MTM may include an area for surgeon or operator input. For example, as shown in FIG. 4B, each MTM 422 a, 422 b may include a pincher assembly 424 a, 424 b. The surgeon grasps a pincher assembly 424 a, 424 b on each MTM 422 a, 422 b, typically with the thumb and forefinger, and can move the pincher assembly to various positions and orientations. When a tool control mode is selected, each MTM 422 is coupled to control a corresponding manipulator arm 406 for the patient side cart 400, as those of ordinary skill in the art are familiar. The pincher assembly is typically used to operate a surgical end effector (e.g., scissors, grasping retractor, needle driver, hook, forceps, spatula, etc.) at the distal end of an instrument 410.

Surgeon's console 420 also can include an image display system 426. In an exemplary embodiment, the image display is a stereoscopic display wherein left side and right side images captured by the stereoscopic endoscope 412 are output on corresponding left and right displays, which the surgeon perceives as a three-dimensional image on display system 426.

The surgeon's console 420 is typically located in the same operating room as the patient side cart 400, although it is positioned so that the surgeon operating the console may be outside the sterile field. One or more assistants may assist the surgeon by working within the sterile surgical field (e.g., to change tools on the patient side cart, to perform manual retraction, etc.). Accordingly, the surgeon may operate remote from the sterile field, and so the console may be located in a separate room or building from the operating room. In some implementations, two consoles 120 (either co-located or remote from one another) may be networked together so that two surgeons can simultaneously view and control tools at the surgical site.

For additional details on the construction and operation of general aspects of a teleoperated surgical system such as described herein, see, e.g., U.S. Pat. Nos. 6,493,608 and 6,671,581, the entire disclosure of each of which is incorporated herein by reference.

Figure 9C:
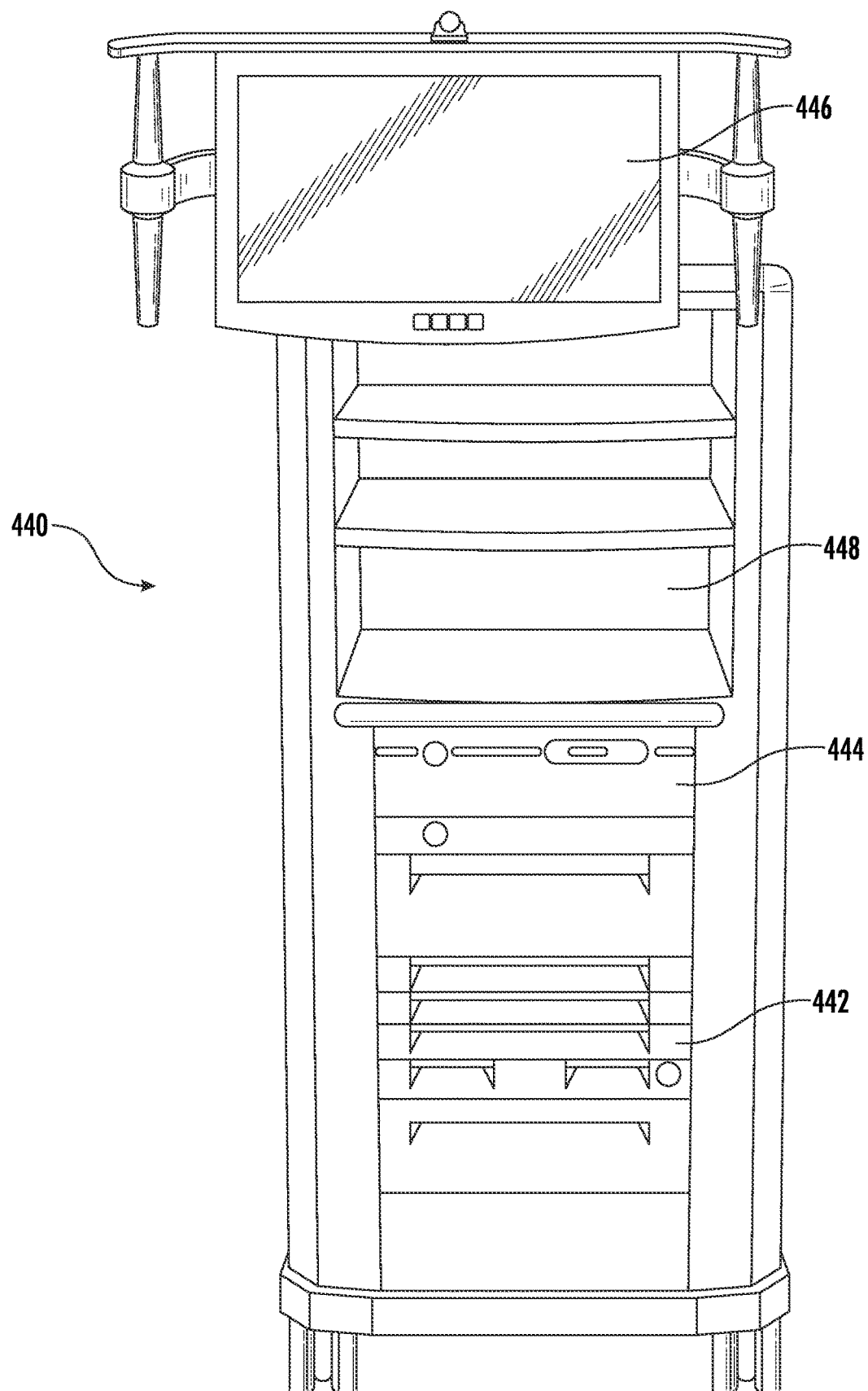
FIG. 9C is a front elevation, diagrammatic view of an exemplary auxiliary control/vision cart of a teleoperated surgical system.

As shown in FIG. 9C, the auxiliary control/vision cart 440 includes an optional display 446 (e.g., a touchscreen monitor), which may be mounted elsewhere, such as on the patient side cart 400. The auxiliary control/vision cart 440 further includes space 448 for optional auxiliary surgical equipment, such as electrosurgical units 444, insufflators 442, and/or other flux supply and control units. The patient side cart 400 (FIG. 9A) and the surgeon's console 420 (FIG. 9B) are coupled via optical fiber communications links to the auxiliary control/vision cart 440 so that the three components together act as a single teleoperated minimally invasive surgical system that provides an intuitive telepresence for the surgeon.

In accordance with various exemplary embodiments, the present disclosure contemplates controlling a surgical instrument such that a gripping force applied by an end effector of the instrument is substantially linear throughout a range of motion of the end effector for a given force applied to a push-pull (drive) rod of the instrument to actuate the end effector.

Figure 10:
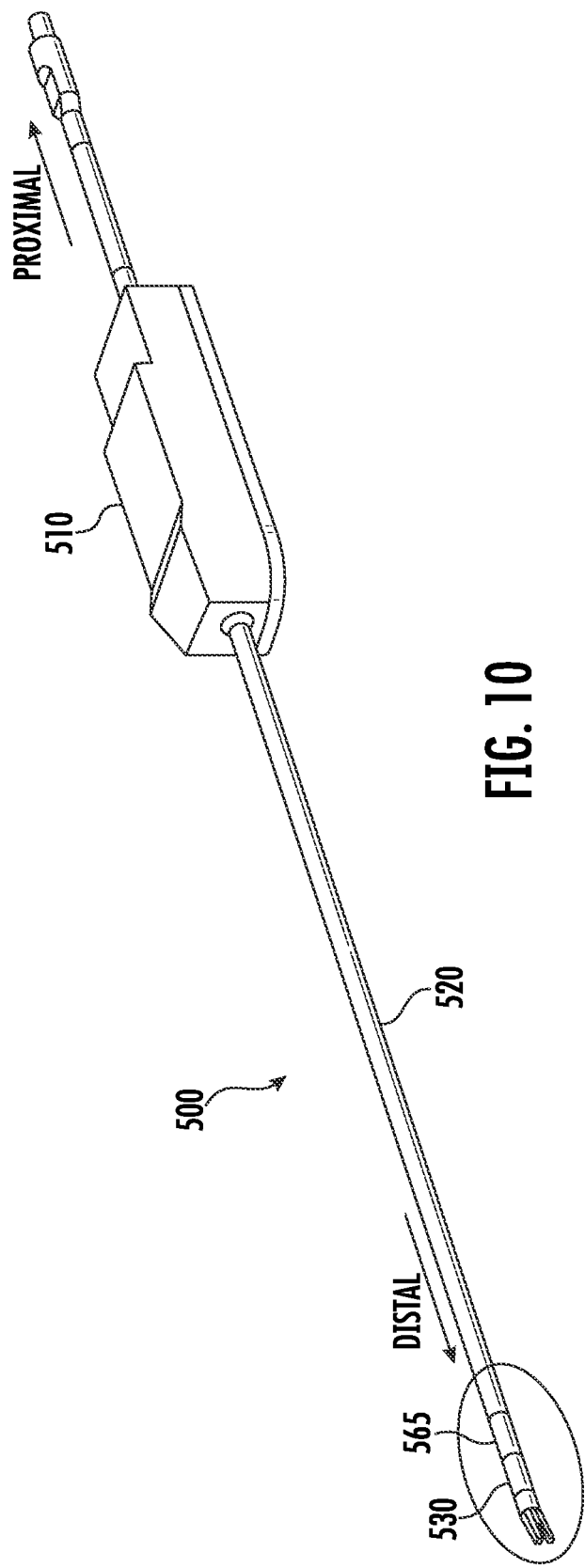
FIG. 10 is a perspective view of a teleoperated surgical instrument usable with an exemplary embodiment of the present teachings.

With reference to FIG. 10, an exemplary embodiment of a teleoperated surgical instrument 500 that may support a previously described end effector of the present disclosure is depicted. As shown in FIG. 10, the instrument 500 generally includes a proximal housing 510 at its proximal end; proximal housing 510 may include an instrument memory or storage device (not shown). The memory can perform a number of functions when the instrument is loaded on the manipulator arm 506. For example, the memory can provide a signal verifying that the instrument is compatible with that particular surgical system. Additionally, the memory may identify the instrument and end effector type (whether it is a scalpel, a needle grasper, jaws, scissors, a clip applier, an electrocautery blade, or the like) to the surgical system so that the system can reconfigure its programming to take full advantage of the instrument's specialized capabilities. As further discussed below, the memory may include specifics on the architecture of the instrument, and include particular values that should be employed in control algorithms, such as tool compliance and gain values.

Proximal housing 510 also may include a force/torque drive transmission mechanism (not shown) for receiving output from motors of the manipulator arm 406, the force/torque drive transmission mechanism transmitting the output from the motors to an end effector 530 of the instrument through an instrument shaft 520 mounted to the transmission mechanism. Exemplary surgical robotic instruments, instrument/manipulator arm interface structures, and data transfer between the instruments and servomechanism is more fully described in U.S. Pat. No. 6,331,181, the full disclosure of which is incorporated herein by reference.

The end effector 530 is disposed at the distal end of the shaft 520 and may be connected thereto by a clevis 535 that supports and mounts the end effector 530 relative to the instrument shaft 520. As embodied herein, the shaft 520 may be a relatively flexible structure that can bend and curve. Alternatively, the shaft 520 may be a relatively rigid structure that does not permit traversing through curved structures. Optionally, in some embodiments, the instrument 500 also can include a multi-DOF articulable wrist structure (not shown) that supports the end effector 530 and permits multi-DOF movement of the end effector in arbitrary pitch and yaw. Those having ordinary skill in the art are familiar with a variety of wrist structures used to permit multi-DOF movement of a surgical instrument end effector.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

Further, this description's terminology is not intended to limit the disclosure. The term "force" is to be construed as encompassing both force and torque, unless otherwise indicated herein or clearly contradicted by context. The terms "tools" and "instruments" are used interchangeably herein to refer to the surgical instruments. As used in this specification and the appended claims, the singular forms "a," "an," and "the," and any singular use of any word, include plural referents unless expressly and unequivocally limited to one referent. The terms "comprising," "having," "including," and "containing" are to be construed as open-ended terms (i.e., meaning "including, but not limited to,") unless otherwise noted. The terms "connected" and "coupled" are to be construed as partly or wholly contained within, attached to, or joined together, even if there is something intervening.

Spatially relative terms—such as "proximal" and "distal—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, the terms "proximal" and "distal" are relative terms, where the term "distal" refers to the portion of the object furthest from an operator of the instrument and closest to the surgical site, such as the opening of the tool cover or the end effector of the instrument. The term "proximal" indicates the relative proximity to the operator of the surgical instrument and refers to the portion of the object closest to the operator and furthest from the surgical site. In this application, an end effector refers to a tool installed at the distal end of an instrument, including but not limited to forceps or graspers, needle drivers, scalpels, scissors, spatulas, blades, and other tools, which may or may not use energy to cauterize tissue (i.e., a monopolar or bipolar tool).

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Various alternatives and modifications can be devised by those skilled in the art without departing from the disclosure. Accordingly, the present disclosure is intended to embrace all such alternatives, modifications and variances. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A surgical instrument for applying surgical clips to tissue, the instrument comprising:
    an end effector including first and second jaws movable between open and closed positions and being configured to receive first and second rows of clips in the open position; and
    a drive element coupled to the end effector and configured to move the jaws between the open and closed positions and to drive the first and second rows of clips into tissue.

2. The surgical instrument of claim 1, wherein the drive element is configured to sequentially form the first and second rows of clips.

3. The surgical instrument of claim 1, wherein the drive element is coupled to a pusher, wherein the pusher is configured to engage the first and second rows of clips into tissue.

4. The surgical instrument of claim 3, wherein the first row of clips is disposed laterally to the second row of clips relative to a longitudinal axis of the end effector.

5. The surgical instrument of claim 4, wherein the drive element is configured to displace the pusher laterally from a first position aligned with the first row of clips to a second position aligned with the second row of clips.

6. The surgical instrument of claim 5, wherein the pusher is moved laterally as the drive element translates the pusher along the longitudinal axis.

7. The surgical instrument of claim 3, wherein the drive element is configured to: (1) translate the drive element distally such that the pusher engages the first row of clips, (2) retract the pusher proximally and displace the pusher laterally, (3) and then translate the drive element distally to engage the second row of clips.

8. The surgical instrument of claim 3, wherein the drive element is configured to close the jaws when the drive element is translated distally and to open the jaws when the drive element is translated proximally.

9. The surgical instrument of claim 3, wherein the pusher is biased towards the first clip upon installation of a clip cartridge.

10. The surgical instrument of claim 3, further comprising a biasing surface configured to laterally translate the pusher towards the second row of clips as the pusher is retracted proximally by the drive element, wherein the biasing surface further comprises a cutout for receiving the drive element, wherein the cutout extends in a lateral direction relative to a longitudinal axis of the instrument, wherein the drive element comprises a flexible cable extending through the cutout and configured for lateral movement through the cutout.

11. The surgical instrument of claim 3, further comprising a clip cartridge configured for positioning between the first and second jaws, wherein the clip cartridge includes first and second rows of clips, wherein the clip cartridge includes an inclined surface configured to laterally displace the pusher to align the pusher with the first row of clips.

12. The surgical instrument of claim 3, wherein the drive element further comprises one or more linkages coupled to one of the first and second jaws, wherein the linkages are configured to close the jaws as the drive element is translated distally.

13. The surgical instrument of claim 1, wherein the drive element is configured for coupling to a robotic teleoperated control system, wherein the robotic teleoperated control system comprises one or more manipulator arms coupled to the drive element and configured to translate the drive element proximally and distally relative to the end effector.

14. A surgical instrument comprising:
    an end effector having a channel for receiving a clip cartridge comprising first and second rows of clips, wherein the end effector comprises first and second jaws movable between open and closed positions;
    a drive member coupled to the end effector and being configured to translate along a longitudinal axis of the end effector to move the jaws between the open and closed positions; and
    wherein the drive member is configured to displace laterally relative to a longitudinal axis of the end effector to engage the cartridge at first and second, laterally spaced, positions on the cartridge.

15. The surgical instrument of claim 14, further comprising an actuator configured to translate the drive member along the longitudinal axis.

16. The surgical instrument of claim 15, wherein the actuator is configured to: (1) translate the drive member distally such that the drive member engages the cartridge at the first position, (2) retract the drive member proximally and displace the drive member laterally, and (3) then translate the drive member distally to engage the cartridge at the second position.

17. The surgical instrument of claim 15, wherein the actuator is configured to close the jaws when the drive element is translated distally and to open the jaws when the drive element is translated proximally.

18. The surgical instrument of claim 14, wherein the drive member is configured to sequentially engage the cartridge at the first and second lateral positions.

19. The surgical instrument of claim 14, wherein the drive member is moved laterally as the drive member translates along the longitudinal axis.

20. The surgical instrument of claim 14, wherein the drive member is biased towards the first position upon installation of the cartridge and further comprising a biasing surface configured to laterally translate the drive member towards the second position as the drive member is retracted proximally by the actuator.

\* \* \* \* \*